United States Patent
Xia et al.

(10) Patent No.: US 8,712,123 B2
(45) Date of Patent: Apr. 29, 2014

(54) ANALYSIS, SECURE ACCESS TO, AND TRANSMISSION OF ARRAY IMAGES

(75) Inventors: Xiongwu Xia, Dayton, NJ (US); Michael Seul, Fanwood, NJ (US); Chiu Chau, Edison, NJ (US); Scott Determan, North Andover, MA (US)

(73) Assignee: Bioarray Solutions, Ltd., Warren, NJ (US)

( * ) Notice: Subject to any disclaimer, the term of this patent is extended or adjusted under 35 U.S.C. 154(b) by 0 days.

(21) Appl. No.: 13/084,869

(22) Filed: Apr. 12, 2011

(65) Prior Publication Data

US 2011/0251093 A1    Oct. 13, 2011

Related U.S. Application Data

(63) Continuation of application No. 11/439,599, filed on May 23, 2006, now Pat. No. 7,940,968, which is a continuation of application No. 10/714,203, filed on Nov. 14, 2003, now Pat. No. 7,526,114.

(60) Provisional application No. 60/426,839, filed on Nov. 15, 2002.

(51) Int. Cl.
*G06K 9/00* (2006.01)

(52) U.S. Cl.
USPC ........... 382/128; 382/129; 382/133; 382/232; 382/294

(58) Field of Classification Search
USPC ................................. 382/128, 129, 232, 294
See application file for complete search history.

(56) References Cited

U.S. PATENT DOCUMENTS

| | | | |
|---|---|---|---|
| 3,329,638 | A | 7/1967 | Blyth |
| 3,574,614 | A | 4/1971 | Carreira |
| 3,790,492 | A | 2/1974 | Fulwyler |
| 3,957,741 | A | 5/1976 | Rembaum et al. |
| 3,982,182 | A | 9/1976 | Hogg |
| 3,989,775 | A | 11/1976 | Jack et al. |

(Continued)

FOREIGN PATENT DOCUMENTS

| | | |
|---|---|---|
| CA | 1248873 | 1/1989 |
| DE | 4035714 | 5/1992 |

(Continued)

OTHER PUBLICATIONS

Nagarajan et al., "Identifying Spots in Microarray Images," *IEEE Transactions on Nanobioscience*, 2002, pp. 78-84, vol. 1.

(Continued)

*Primary Examiner* — Wesley Tucker
(74) *Attorney, Agent, or Firm* — Womble Carlyle Sandridge & Rice, LLP

(57) ABSTRACT

Systems and methods are provided the autocentering, autofocusing, acquiring, decoding, aligning, analyzing and exchanging among various parties, images, where the images are of arrays of signals associated with ligand-receptor interactions, and more particularly, ligand-receptor interactions where a multitude of receptors are associated with microparticles or microbeads. The beads are encoded to indicate the identity of the receptor attached, and therefore, an assay image and a decoding image are aligned to effect the decoding. The images or data extracted from such images can be exchanged between de-centralized assay locations and a centralized location where the data are analyzed to indicate assay results. Access to data can be restricted to authorized parties in possession of certain coding information, so as to preserve confidentiality.

19 Claims, 15 Drawing Sheets

(56) References Cited

U.S. PATENT DOCUMENTS

| | | |
|---|---|---|
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | Van Ness et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |

(56) References Cited

U.S. PATENT DOCUMENTS

| | | |
|---|---|---|
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Willey |
| 5,643,765 A | 7/1997 | Willey |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | Van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforov et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,031,910 A * | 2/2000 | Deindl et al. ............... 380/255 |
| 6,033,547 A | 3/2000 | Trau et al. |
| 6,043,354 A | 3/2000 | Hillebrand et al. |
| 6,048,690 A | 4/2000 | Heller |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |

(56) References Cited

U.S. PATENT DOCUMENTS

| | | |
|---|---|---|
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauvar et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 * | 6/2005 | Ravkin et al. ............... 435/6.11 |
| 6,942,968 B1 | 9/2005 | Dickinson et al. |
| 6,955,751 B2 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |

(56) References Cited

U.S. PATENT DOCUMENTS

| | | |
|---|---|---|
| 2001/0044531 A1 | 11/2001 | McGall et al. |
| 2001/0046602 A1 | 11/2001 | Chandler et al. |
| 2001/0049095 A1 | 12/2001 | Webster |
| 2002/0006634 A1 | 1/2002 | Han et al. |
| 2002/0010679 A1* | 1/2002 | Felsher .......................... 705/51 |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |
| 2003/0087228 A1 | 5/2003 | Bamdad et al. |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2003/0232379 A1* | 12/2003 | Amorese et al. .................. 435/6 |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| GB | 2 058 379 A | 4/1981 |
| JP | 62265567 | 11/1987 |
| JP | 03-236777 | 10/1991 |
| WO | WO8911101 | 5/1989 |
| WO | WO 9109141 | 6/1991 |
| WO | WO 9119023 | 12/1991 |
| WO | WO 9210092 | 6/1992 |
| WO | WO 9325563 | 6/1992 |
| WO | WO 9302360 | 2/1993 |
| WO | WO 9306121 | 4/1993 |
| WO | WO 9324517 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO 9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9806007 | 12/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0026920 | 1/2000 |
| WO | WO 0007019 | 2/2000 |
| WO | WO 0013400 | 3/2000 |
| WO | WO 0020593 | 4/2000 |
| WO | WO 0022172 | 4/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |

(56) References Cited

FOREIGN PATENT DOCUMENTS

| WO | WO 01/56216 A2 | 1/2001 |
|---|---|---|
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 01/98765 | 12/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 02/35441 A2 | 5/2002 |
| WO | WO 02/37209 A1 | 5/2002 |
| WO | WO 0235441 | 5/2002 |
| WO | WO 0237209 | 5/2002 |
| WO | WO02057496 | 7/2002 |
| WO | WO02058379 | 7/2002 |
| WO | WO02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |
| WO | WO2010026038 | 3/2010 |
| WO | WO2010098765 | 9/2010 |
| WO | WO 2010143678 | 12/2010 |

OTHER PUBLICATIONS

Stevens et al., "Imaging and Analysis of Immobilized Particle Arrays," *Analytical Chemistry*, 2003, pp. 1147-1154, vol. 75.

Armstrong et al., "Suspension arrays for high throughput, multiplexed single nucleotide polymorphism genotyping" Cytometry. vol. 40:102-108 (2000).

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B. -Y. Ha et al., "Counterion-Mediated Attraction between Two Like-Charged Rods, " Physical Review Letters, Aug. 18, 1997, vol. 79, No. 7, pp. 1289-1292.

A. Hatch, et al., "Diffusion Immunoassay in Polyacrylamide Hydrogels". Micro Total Analysis Systems, pp. 571-572 (2001).

Aho et al., "Efficient String Matching: An Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369-375 (May 2006).

Albrecht et al., "Photo and electropatterning of hydrogel-encapsulated living cell arrays", Lab on a Chip, vol. 5, Issue 1, pp. 111-118 (2004).

Alford, R. L., "DNA Analysis in forensics, disease and animal/plant identification". Current Opinions in Biotechnology, vol. 5(1), pp. 29 - 33 (1994).

Al-Soud, W. A., "Purification and Characterization of PCR-Inhibitory Components in Blood Cells". Journal of Clinical Microbiology, vol. 39, No. 2, pp. 485 - 493 (Feb. 2001).

Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).

Ambruso, D. R., et al., "Experience with donors matched for minor blood group antigens in patients with sickle cell anemia who are receiving chronic transfusion therapy", TRANSFUSION, vol. 27, No. 1, 1987, pp. 94-98.

Zhang, Y., et al., "Reproducible and inexpensive probe preparation for oligonucleotide arrays". Nucleic Acids Research, vol. 29, No. 13, pp. E66-6 (Jul. 1, 2001).

Arenko, et al., "Protein microchips: Use for immunoassay and enzymatic reactions". Analytical Biochemistry, vol. 278, pp. 123-131 (2000).

Assie et al., Correlation between low/high affinity ratios for 5-HT Receptors and Intrinsic Activity, European Journal of Pharmacology, vol. 386, pp. 97-103 (1999).

Bakewell et al., "Characterization of the dielectrophoretic movement of DNA in micro-fabricated structures", Institute of Phyics Conference Series (1999) Electrostatics (1999).

Balass et al. "Recovery of high-affinity phage from a Nitrostretavidin matrix in phage-display technology". Analytical Biochemistry. vol. 243: 264-269 (1996).

Baldwin, et al., "Phosphorylation of gastrin-17 by epidermal growth factor-stimulated tyrosine kinase". Nature, vol. 44, pp. 2403-2404 (1998).

Bandeira-Melo, C., et al., "EliCell: A gel-phase dual antibody capture and detection assay to measure cytokine release from eosinophils". Journal of Immunological Methods, vol. 244, pp. 105-115 (2000).

Bao, Y. P., et al., "Detection of Protein Analytes via Nanoparticle-Based Bio Bar Code Technology". Anal. Chem., vol. 78, pp. 2055-2059 (2006).

Barany, Francis, "Genetic Disease Detection and DNA Amplification using Cloned Thermostable Ligase". Proceedings of the National Academy of Sciences of the United States of America, vol. 88, pp. 189-193 (Jan. 1991).

Barnard et al. "A fibre-optic chemical sensor with descrete sensing sites". Nature, vol. 353:338-340 (1991).

Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).

Battersby et al., "Toward Larger Chemical Libraries: Encoding with Fluorescent Colloids in Combinatorial Chemistry". J. Amer Chem Soc, vol. 122, pp. 2138-2139 (2000).

Baumgarth N. et al., A practical approach to multicolor flow cytometry for immunophenotyping, J. Immunological Methods, 2000, pp. 77-97, vol. 243.

Bavykin, S.G., et al., "Portable system for microbial sample preparation and oligonucleotide microarray analysis". Appl. Environmental Microbiol. 67(2), 922-928 (2001).

Beatty et al. "Probability of Finding HLA-mismatched Related or Unrelated Marrow or Cord Blood Donors", Human Immunology, 2001, vol. 61, pp. 834-840.

Beebe et al., "Functional Hydrogel structures for autonomous flow control inside microfluidic channels". Nature, vol. 404, No. 6778, pp. 588-590 (Apr. 6, 2000).

Beiboer, S. W., et al., "Rapid genotyping of blood group antigens by multiplex polymerase chain reaction and DNA microarray hybridization" 45 Transfusion 667-679 (2005).

Bennett, P. R., et al., "Prenatal Determination of Fetal RhD Type by DNA Amplification". The New England Journal of Medicine, vol. 329, No. 9, pp. 607-610 (Aug. 26, 1993).

Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).

(56) References Cited

OTHER PUBLICATIONS

Bessetti, J., "An introduction to PCT Inhibitors". Profiles in DNA-PCR Inhibition, pp. 9-10 (Mar. 2007).
Bickel, P. J., "Discussion of the Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". Bio Techniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso, "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and Escheria coli exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". Vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays", vol. 21, pp. 15-19 (Jan 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, page est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/pcrcond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).

(56) References Cited

OTHER PUBLICATIONS

Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a smalll dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G. , "Fuzzy Nanoassemblies: Towared Layered Polymeric Multicomposites". Science, vol. 277, pp. 1232-1237 (Aug 29, 1997).
Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligunucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb 15, 1991).
Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).
Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.

(56) References Cited

OTHER PUBLICATIONS

Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2000;7(10):569-79.
Gustafsdottir, S. M., "In vitro analysis of DNA—protein interactions by proximity ligation". PNAS, vol. 104, No. 9, pp. 3067-3072 (Feb. 2007).
Haab et al. Single Molecule Fluorescence Burst Detection of DNA Fragments Separated by Capillary Electrophoresis. Analytical Chemistry, vol. 67 (No. 18) : 3253-3256 (1995).
Hacis et al., "Resequencing and mutational analysis using oligonucleotide microarrays", Nature America; 21 : 42-47 (1999).
Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).
Hashimi et al., "A Flexible Array format for large-scale, rapid blood group DNA typing". Transfusion, Published Online Apr. 6, 2004, vol. 45, Issue 5, pp. 680-688 (May 2005).
Hashmi, G., et al, "Determination of 24 minor red blood cell antigens for more than 2000 blood donors by high-throughput DNA analysis". Transfusion, vol. 47, No. 4, pp. 736-747 (Apr. 2007).
Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan 15, 1997).
Heinrich, et al., "Interleukin-6-type Cytokine Signaling through the gp 130/Jak/STAT pathway". Biochem J, vol. 334, pp. 297-314 (1998).
Helgesen, et al., "Aggregation of magnetic microspheres: experiements and simulations". Physical Review Letters, vol. 61, No. 15, pp. 1736-1739 (1998).
Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).
Hermanson, G. T., "Nucleic Acid and Oligonucleotide Modification and Conjugation". Bioconjugate Techniques, Academic Press, Chapter 17, pp. 639-671 (Jan. 15, 1996).
Yershov et al., "DNA analysis and diagnostics on oligonulceotide microchips". Proceedings of the National Academy of Sciences of the United States of America, vol. 93, No. 10, pp. 4913-4918 (May 14, 1996).
Hiller, J., et al., "Reversibly erasable nanoporous anti-reflection coatings from polyelectrolyte multilayers". Nature Materials, vol. 1, pp. 59-63 (Sep. 2002).
Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).
Hizume, et al., "Tandem repeat DNA localizing on the proximal DAPI bands of chromosomes in Larix, pinaceae". Genome, vol. 45, pp. 777-783 (2002).
Holtz, J., et al., "Intelligent Polymerized Crystalline Colloidal Array: Novel Sensor Materials", Analytical Chemistry, vol. 70, No. 4, pp. 780-791 (1998).
Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).
Huff et al., "Technical Milestone: Development of the Logical Observation Identifier Names and Codes (LOINC) Vocabulary". JAIMA, vol. 5, pp. 276-292 (1998).
Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).
Ide et al., "Synthesis and damage specificity of a novel probe for the detection of abasic sites in DNA", Biochemistry. vol. 32: 8276-8283 (1993).
Ito, Y., et al., "Patterned Immobilization of Thermoresponsive Polymer", Langmuir, vol. 13, pp. 2756-2759 (1997).
Iwayama, et al., "Optically Tunable Gelled Photonic Crystal Covering Almost the Entire Visible Light Wavelength Region", Langmuir (2002).
Jackman, R. J., et al., "Using Elastomeric Membranes as Dry Resists and for Dry Lift-Off", Langmuir, vol. 15, pp. 2973-2984 (1999).
Jeon, N. L., et al., "Patterned polymer growth on silicon surfaces using microcontact printing and surface-initiated polymerization", Applied Physics Letters, vol. 75, No. 26, pp. 4201-4203 (1999).
John C. Guatelli et al., "Isothermal, in vitro amplification of nucleic acids by a multienzyme reaction modeled after retroviral replication, "Proc. Nat'l Academy of Science USA, vol. 87: pp. 1874-1878 (1990).
Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).
Jones et al., "Constraint, Optimization, and Hierarchy: Reviewing Stereoscopic Correspondence of Complex Features". Computer Vision and Image Understanding, vol. 65, No. 1, pp. 57-78 (1997).
Jones et al., "Dielectrophoretic liquid actuation and nanodroplet formation", Journal of Applied Physics, vol. 89, No. 2, pp. 1441-1448 (Jan. 15, 2001).
Kakabakos et al. "Immobilization of Immunoglobulins onto Surface-treated and Untreated Polystyrene Beads for Radioimmunoassays" Clin. Chem. 36 (1990), 492-496.
Kalinina, O., et al., "A core-shell Approach to Producing 3D Polymer Nanocomposites", Macromolecules, vol. 32, pp. 4122-4129 (1999).
Kamholz, et al., "Optical measurement of transverse molecular diffusion in a microchannel". Biophysical Journal, vol. 80, pp. 1967-1972 (2001).
Kamm, R. C., et al. "Nucleic Acid Concentrations in Normal Human Plasma". Clinical Chemistry, vol. 18, pp. 519-522 (1972).
Kandimalla et al., "Cyclicons" as Hybridization-Based Fluorescent Primer-Probes: Bioorganic & Medicinal Chemistry 8 (2000) 1911 to 1916.
Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).
Klintschar, et al., "Genetic variation at the STR loci D12S391 and CSF1PO in four populations from Austria, Italy, Egypt and Yemen". Forensic Sci. Int. vol. 97:37-45 (1998).
Kim, E., et al., "Polymer microstructures formed by moulding in capillaries", Nature, vol. 376, pp. 581-584 (1995).
Knipper, et al., Accession No. AF221125.1.1 on Electronic Database at NCBI (Feb. 16, 2000).
Koch et al., "PNA-Peptide Chimerae", Tetrahedron Letters, vol. 36, pp. 6933-6936 (1995).
Koh, et al., "Molding of Hydrogel Microstructures to Create Multiphenotype Cell Microarrays". Analytical Chemistry (2003).
Koh, et al., "Poly(ethylene glycol) Hydrogel Microstructures Encapsulating Living Cells". Langmuir, vol. 18, pp. 2459-2462 (2002).
Kolch. "Meaningful Relationships: The Regulation of the Ras/Raf/MEK/ERK pathway by protein interactions". Biochem J, vol. 351, pp. 289-305 (2000).
Kotov, N., et al., "Layer-by-Layer Self-Assembly of Polyelectrolyte-Semiconductor Nanoparticle Composite Films". J. Phy Chem, vol. 99, pp. 13065-13069 (1995).
Krausa et al. "A Comprehensive PCR-ssP typing system for identification of HLA-A locus alleles", Tissue Antigens, 47 (3) : 237-244 (1996).
Krsko, P., et al., "Electron-Beam Surface Patterned Poly(ethylene glycol) Microhydrogels". Langmuir, vol. 19, pp. 5618-5625 (2003).

(56) References Cited

OTHER PUBLICATIONS

Krutzik P.O. et al., "Fluorescent cell barcoding in flow cytometry allows high-throughput drug screening and signal profiling". Nature Methods, vol. 3, No. 5, pp. 361-368 (2006).

Kubo et al., "A Novel Sensitive and specific assay for abasic sites, the most commonly produced DNA lesion". Biochemistry, vol. 13:3703-3708 (1992).

Kumacheva, E., et al., "Three-dimensional Arrays in Polymer Nanocompositites", Advanced Materials, vol. 11, No. 3, pp. 231-234 (1999).

Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).

Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).

Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).

Lagerholm et al., "Theory for Ligand Rebinding at Cell Membrane Surfaces," Biophysical Journal (1998), vol. 74, pp. 1215-1228.

Lamb, D. J., et al., "Modification of Natural and Artificial Polymer Colloids by Topology-Controlled Emulsion Polymerization". Biomacromolecules, vol. 2, No. 2, pp. 518-525 (2001).

Lander, E. S. "The New Genomics: Global Views of Biology". Sciences, vol. 274, No. 5287, pp. 536-539 (Oct. 25, 1996).

Lander, E. S., et al., "Array of Hope". Nature Genetics Supplement, Perspective, vol. 21, pp. 3-4, (Jan. 1999).

Latour, P., et al., "Polymorphic Short Tandem Repeats for Diagnosis of the CharotMarie-Tooth IA Duplication". Clinical Chemistry, vol. 47, pp. 829-837 (2001).

Lau, F. Y., et al., "Provision of phenotype-matched blood units: no need for pre-transfusion antibody screening", HAEMATOLOGICA, vol. 86, No. 7, Jul. 2001, pp. 742-748.

Lee et al. "Quantitation of residual WBCs in filtered blood components by high-throughput, real time kinetic PCR", Blood Components, transfusion, vol. 42, pp. 87-93 (Jan. 2002).

Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).

Lee, H. J., et al., "Fabricating RNA Microarrays with RNA-DNA Surface Ligation Chemistry". Analytical Chemistry, vol. 77, No. 23, pp. 7832-7837 (Dec. 1, 2005).

Lee, S., et al., "Control of Core-Shell Latex Morphology". Polymer Latexes, ACS Symposium, American Chemical Society, pp. 234-253 (1992).

Lemieux: "high throughput single nucleotide polymorphism genotyping technology" Current Genomics. vol. 1:301-311 (2000).

Lhomme et al. "Abasic DNA structure, reactivity and recognition". Biopolymers. vol. 52 : 65-83 (1999).

Li, A., et al., "Multiplexed analysis of polymorphisms in the HLA gene complex using bead array chips". Tissue Anitigens, vol. 63, pp. 518-528 (2004).

Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).

Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235-246 (1999).

Liebert, M. R., et al., "Dynamics of the holes in human erythrocyte membrane ghosts". J. Biological Chemistry, vol. 257, No. 19, pp. 11660-11666 (1982).

Lin et al. "Raman Studies of Bovine Serum Albumin" . Biopolymers 15:203-218 (1976).

Lindahl et al., "Rate of depuriniation of native deoxyribonucleic acid". Biochemistry. vol. 11, No. 19: 3610-1617 (1972).

Lindahl et al., "Rate of chain breakage at apurinic sites in double-stranded deoxyribonclueic acid" Biochemistry, vol. 11, No. 19:3618-3623 (1972).

Lipshutz, R. J., et al., "High Density Synthetic Oligonucleotide Arrays". vol. 21, pp. 20-24 (Jan. 1999).

Liu, et al., "Development of a Carbon Dioxide-Base Microencapsulation Technique for Aqueous and Ethanol-Based Latexes". Langmuir (2002).

Liu, V, et al, "Three-Dimensional Photopatterning of Hydrogels Containing Living Cell". Biomedical Microdevices, vol. 4, No. 4, pp. 257-266 (2002).

Lofas, et al., "Methods for site controlled coupling to carboxymethyldextran surfaces in surface plasmon resonance sensors". Biosensors & Bioelectronics, vol. 10, pp. 813-822 (1995).

Loomans, E., et al., "Assessment of the functional affinity constant of monoclonal antibodies using an improved enzyme-linked immunosorbent assay". Journal of Immunological Methods, vol. 184, pp. 207-217 (1995).

Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).

Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).

Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multilayers of SiO2 and Other Nanoparticles and Polyions". Langmuir, vol. 13, pp. 6195-6203 (1997).

MacBeath et al., "Printing proteins as microarrays for high-throughput function determination". Science, vol. 289; pp. 1760-1763 (Sep. 8, 2000).

Maldonado-Rodriguez et al., "Hybridization of glass-tethered oligonucleotide probes to . . . ", Molecular Biotechnology, vol. 11, No. 1, pp. 1-12 (1999).

Marras et al., Multiplex detection of single-nucleotide variations using molecular beacons: Genetic Analysis: Biomolecular Engineering 14 (1999) 151-156.

Marsh, S. G. E., et al., The HLA Facts Book, "HLA Typing at the DNA Level", Academic Press, Chapter 6, pp. 37-39 (2000).

Martin, M., et al. "A Method for Using Serum or Plasma as a Source of DNA for HLA Typing". Human Immunology, vol. 33, pp. 108-113 (1992).

Martinell, J. et al., "Three mouse models of human thalassemia", Proc. Natl. Acad. Sci, USA. Aug. 1981, vol. 78, No. 8, pp. 5056-5060.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).

Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).

Matthews et al., "Biochemistry: A Short Course". New York: John Wiley & Sons, Inc, p. 25 (1997).

Maxam et al.,"A new method for sequencing DNA," Proc. Natl. Acad. Sci. USA. vol. 74, No. 2, pp. 560-564, Feb. 1977.

McCloskey, et al., "Magnetic Cell Separation: Characterization of Magnetophoretic Mobility". Anal. Chem., vol. 75, pp. 6868-6874 (2003).

McCloskey, et al., "Magnetophoretic Mobilities Correlate to Antibody Binidng Capacities". Cytometry, vol. 40, pp. 307-315 (2000).

(56) References Cited

OTHER PUBLICATIONS

Mei et al. "Genome-wide Detection of Allelic Imbalance Using Human SNPs and High-Density DNA Arrays". Genome Research. vol. 10, pp. 1126-1137 (2000).
Michael, et al., "Randomly ordered addressable high-density optical ssensor arrays". Anal. Chem, vol. 70, pp. 1242-1248 (1999).
Micheletto et al., "A simple method for the production of a two-dimensional ordered array of small latex particles". Langmuir, vol. 11, pp. 3333-3336 (1995).
Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).
Moore, et al., "The use of magnetite-doped polymeric microspheres in calibrating cell tracking velocimetry". J. Biochem. Biophys. Methods, vol. 44, pp. 115-130 (2000).
Morag et al. "Immobilized nitro-avidin and nitro-streptavidin as reusable affinity matrices for application in avidin-biotin technology". Analytical Biochemistry. vol. 243: 257-263 (1996).
Mori, et al., Computer program to predict liklihood of finding an HLA-matched donor: Methodology, validation, and application. Biology of Blood and Marrow Transplantation, vol. 2, pp. 134-144 (1996).
Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.
Muller et al., "Gene and Haplotype Frequencies for the Loci HLA-A, HLB-B, and HLA-DR Based on Over 13,000 German Blood Donors". Human Immunology, 2003, 64: 137-151.
Mullis et al. Specific Synthesis of DNA in Vitro via a Polymerase-Catalyzed Chain Reaction Methods in Enzymology, 1987; vol. 155, pp. 335-350.
Nagarajan et al., "Identifying Spots in Microarray Images", IEEE Transactions on Nanobioscience, vol. 1, No. 2, pp. 78-84 (Jun. 2002).
Nagayama et al., "Fabrication of two-dimensional colloidal arrays". Phase Transitions, vol. 45, 185-203 (1993).
Nam, J., et a., "Colorimetric Bio-Barcode Amplification Assay for Cytokines". Anal. Chem., vol. 77, pp. 6985-6988 (2005).
Nau et al., "A Command Processor for the Determination of Specificities fro Matrices of Reactions Between Blood Cells and Antisera". Computers and Biomedical Research, vol. 10, pp. 259-269 (1977).
Nazarenko et al. (2002) Multiplexed quantitiative PCR using self-quenched primers labeled with a single fluorophore. Nucleic Acids Research, 30 (9), e37.
Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).
Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).
Nygren, "Molecular Diagnostics of Infectious Diseases" Royal Institute of Technology Department of Biotechnology, Stockholm 2000, pp. 1-68.
Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.
Okubo, and Yamashita. "Thermodynamics for the preparation of micorn-sized, monodispersed highly monomer-'absorbed' polymer particles utilizing the dynamic swelling method." Colloids and Surfaces, 1999:153-159.
Okubo et al., "Preparation of micron-size monodisperse polymer particles by seeded polymerization utilizing the dynamic monomer swelling method". Colloid and Polymer Science, vol. 269, No. 3, pp. 222-226 (1991).
Olejnik et al., "Photocleavable biotin phosphoramidite for 5'-end-labeling, purification & phosphorylation of oligonucleotides", Nucleic Acids Research 1996, vol. 24, 2:361-366.
Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).
Olson et al. "A common langauage for physical mapping of the human genome". Science, vol. 245, pp. 1434-1435 (1989).
Otero, T. F., et al., "Electrochemically initiated acrylic acid/acrylamide copolymerization", J. Electroanal. Chem., vol. 256, pp. 433-439 (1998).
Otero, T. F., et al., "Electroinitiated polymerization of acrylamide in DMG: Attempts at an interfacial model", J. Electroanal. Chem., vol. 304, pp. 153-170 (1991).
Pastinen, et al., "A System for specific, high-throughput genotyping by allele-specific primer extension on microarrays". Genome Res., vol. 10, pp. 1031-1042 (2000).
Peter, C., et al., "Optical DNA-sensor chip for real-time detection of hybridization events". Fresenius J. Anal. Chem, vol. 371, pp. 120-127 (Jun. 2001); Published online Springer-Verlay 2001.
Wilson, M.R., et al., "A New Microsphere-based Immunofluorescence Assay for Antibodies to Membrane-associated Antigens". Journal of Immunological Methods, vol. 107, pp. 231-237 (1988).
Peterson, et al., "Fiber Optic pH probe for physiological use". Anal. Chem. vol. 52, 864-869 (1980).
Peterson, et al., "Fiber Optic Sensors for Biomedical Applications". Science, vol. 13; pp. 123-127 (1984).
Peytavi et al., "Correlation between microarray DNA hybridization efficiency and the position of short capture probe on the target nucleic acid". Biotechniques, vol. 39, No. 1, pp. 89-96 (2005).
Pooga, M., et al., "Cell-Penetrating constructs regulate galanin receptor levels and modify pain transmission in vivo" Nature Biotechology, vol. 16, pp. 857-861 (1998).
Pope. "Fiber optic chemical microsensors employing optically active silica microspheres". SPIE, vol. 2388; pp. 245-256 (1995).
Prati D. et al., DNA Enzyme Immunoassay of the PCR-Amplified HLA-DQ Alpha Gene for Estimating Residual Leukocytes in Filtered Blood Clinical and Diagnostic Laboratory Immunilogy, Mar. 1995, p. 182-185.
Pregibon et al., "Magnetically and Biologically Active Bead-Patterned Hydrogels", Langmuir, vol. 22, pp. 5122-5128 (2006).
Preza, "Phase Estimation using rotational diversity for different interference contrast microscopy". Dissertation presented to the Washington University Server Institute of Technology, Department of Electrical Engineering; St. Louis MO (Aug. 1998).
Proudnikov et al., "Chemical methods of DNA and RNA florescent labeling". Nucleic Acids Research. vol. 24, No. 22: 4535-4542 (1996).
Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).
Quon, R., et al., "Measurement of the Deformation and Adhesion of Rough Solids in Contact". J. Phys. Chem., vol. 103, pp. 5320-5327 (1999).
Rabbany et al., "Assessment of hetrogeneity in antibody displacement reactions". Anal Chem, vol. 69, pp. 175-182 (1997).
Radtchecnko et al., "Core-shell structures formed by the solvent-controlled precipitation of luminescent ScTe nanocrystals on latex spheres". Advanced Materials, vol. 13, No. 22, pp. 1684-1687 (2001).
Radtkey et al., "Rapid, high-fidelity analysis of simple sequence repeats on an electronically active DNA microchip". Nucleic Acids Research, vol. 28, No. 7, p. e17 (2000).
Ramsay, G., "DNA Chips: State-of-the-Art". Nature Biotechnology, vol. 16, pp. 40-44 (Jan. 1998).

(56) References Cited

OTHER PUBLICATIONS

Reddy et al., "Determination of the Magnetic Susceptibility of Labeled Particles by Video Imaging". Chemical Engineering Science, vol. 51, No. 6, pp. 947-956 (1996).
Reid M.E., et al., "Novel Dombrock blood group genetic variants . . . ", Blood (ASH Annual Meeting Abstract) 2004, 104: Abstract 383.
Relogio, A. et al., "Optimization of oligonucleotide-based DNA microarrays", Nucl. Acids Res., vol. 30, e51, pp. 1-10 (2002).
Richardson et al., "The use of coated paramagnetic particles as a physical label in a magneto-immunassay". Biosensors & Bioelectronics, vol. 16, pp. 989-993 (2001).
Richardson, et al., "A novel measuring system for the determination of paramagnetic particle lables for use in magneto-immunoassays". Biosensors & Bioelectronics, vol. 16, pp. 1127-1132 (2001).
Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).
Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al., "Precipitation with Ethanol or Isopropanol", Concentrating Nucleic Aicds, Molecular Cloning vol. 3, pp. E3-E4 and E.10-E.15 (1989).
Sano, T, et al., "Immuno-PCR: Very Sensitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when Linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al., "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem, Jul. 2004; 204 (1):22-5).

Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).
Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).
Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262: 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham , P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).

(56) References Cited

OTHER PUBLICATIONS

Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).
Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvilli, S.A. et al. "Adsorption of human serum albumin: Dependence on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucleotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genome-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model For the effects of time and temperature onthe gelation time of BSA gels." Macromolecules. vol. 30:4845-4854 (1997).
Tokumasu F. et al, Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).

Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells" , Malaria Journal (2004) pp. 1-7 from http://www.malariajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).
Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry, vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., Working Party of the BCSH: "Guidelines for compatibility procedures in blood transfusion laboratories", Transfusion Medicine, vol. 14, pp. 59-73 (2004).
Yamashita et al., "Thermodynamics for the preparation of micronsized, monodispersed highly monomer absorbed polymer particles utilizing the dynamic selling method". Colloids and Surfaces, vol. 153, pp. 153-159 (1999).
Yao et al., "Molecular-beacon-based array for sensitive DNA analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).

(56) References Cited

OTHER PUBLICATIONS

Friedli, Interaction of SWP with Bovine Serum Albumin (BSA) and Soluble Wheat Protein (SWP) (7 pages) downloaded http://www.friedli.com/research/PhD/chapter5a.html.

Hermanson, Greg T., "Zero Length Cross-Linkers"; Bioconjugate Techniques; Academic Press, pp. 170-176 (1996).

Hermanson, Greg T., "Bioconjugate Techniques", Bioconjugate Techniques; Academic Press, San Diego, 430-33, (1996).

MacBeath et al., "Printing proteins as microarrays for high-throughput function determination," Science vol. 289: 1760-1763 (2000).

Tobitani et al. "Heat-induced gelation of globular proteins 2. Effect of environmental factors on single-component and mixed-protein gels," Macromolecules; vol. 30: 4855-4862 (1997).

Wittemann et al., "Interaction of Proteins with Spherical Polyelectrolyte Brushes" (Polyer Institute, University of Karisruhe, Karisruhe, Germany) Poster Oct. 2001.

Hogue et al., "Extraction of DNA from Serum for High-Throughput Genotyping: Findings from Pilot Studies Within the Prostate Cancer Prevention Trial," Basic and Translational Science, Urology 71 (5), pp. 967-970 (2008).

* cited by examiner

FIG. 9A
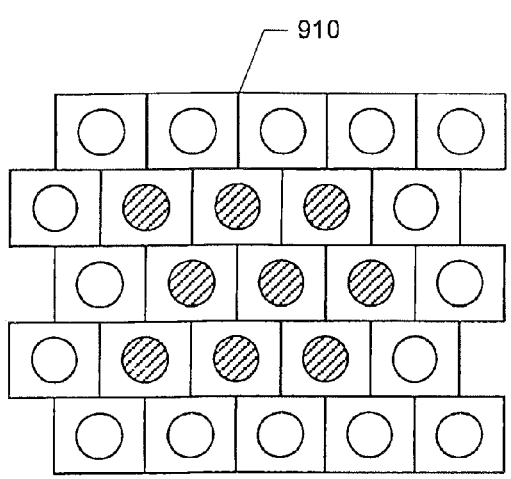
FIG. 9B
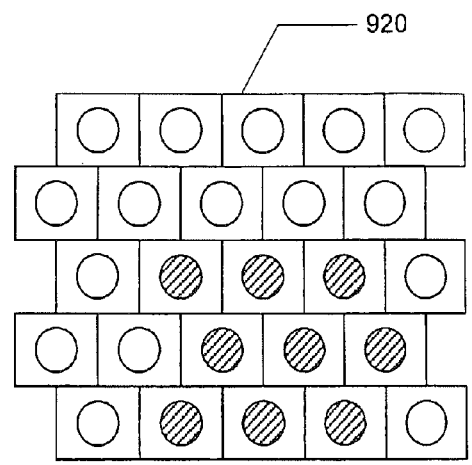
FIG. 9C
| X |   | X |
|---|---|---|
| X | X | X |
| X |   | X |

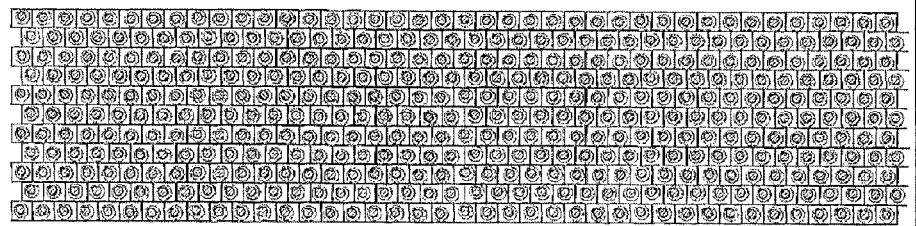
FIG. 13A
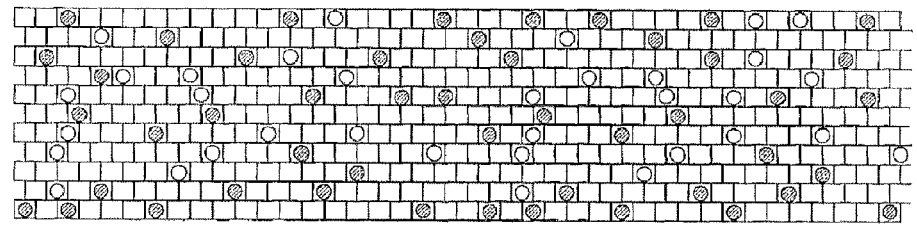
FIG. 13B
FIG. 14
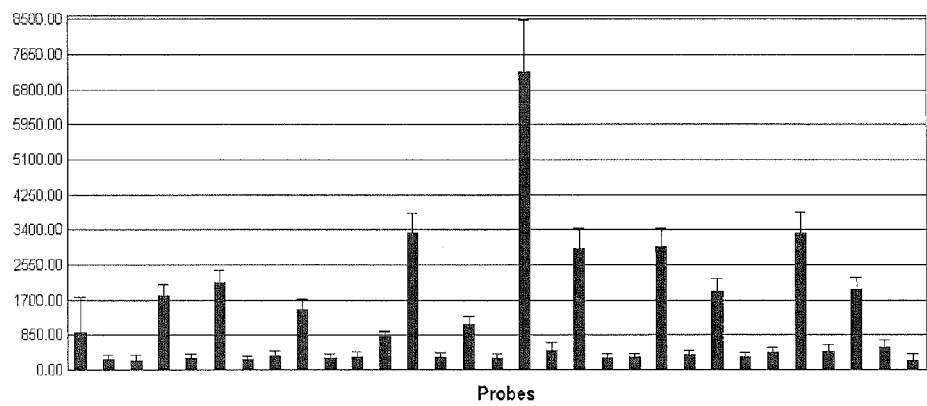

US 8,712,123 B2

ANALYSIS, SECURE ACCESS TO, AND TRANSMISSION OF ARRAY IMAGES

RELATED APPLICATIONS

This application is a continuation of U.S. patent application Ser. No. 11/439,599, filed May 23, 2006, which is a continuation of U.S. patent application Ser. No. 10/714,203, now issued as U.S. Pat. No. 7,526,114, filed Nov. 14, 2003, which claims priority to U.S. Provisional Application No. 60/426,839, filed Nov. 15, 2002, the entire contents of each of which are incorporated herein by reference in their entireties.

BACKGROUND

Recent rapid advances in molecular biology have created more demand for high volume testing based on the need to screen ever larger compound libraries, validate ever increasing numbers of genetic markers and test ever more diversified patient populations. This has led to the development of new array formats, particularly for nucleic acid and protein-protein interaction analysis, which increase parallel processing by performing requisite assays in a "multiplexed" format.

Conventionally, such assays are performed by producing arrays of nucleic acids and antibodies by way of "spotting" or "printing" of aliquot solutions on filter paper, blotting paper or other substrates. However, notwithstanding their widespread current use in academic research targeting gene expression and protein profiling, arrays produced by spotting have shortcomings, particularly in applications placing high demands on accuracy and reliability and where large sample volume and high throughput is required. In another more recently developed technique, spatially encoded probe arrays are produced by way of in-situ photochemical oligonucleotide synthesis. However, this technology is limited in practice to producing short oligonucleotide probes—and requiring alternative technologies for the production of cDNA and protein arrays—and precludes rapid probe array customization given the time and cost involved in the requisite redesign of the photochemical synthesis process.

In addition to these inherent difficulties in assay performance, spatially encoded arrays produced by methods of the art generally produce data of such poor quality that specialized scanners are required to extract data of useable quality. Commercial systems available for this purpose require confocal laser scanning—a slow process which must be repeated for each desired signal color—and limit the spatial resolution to ~5 μm.

In order to resolve many of the problems associated with diagnostic and analytical uses of "spotted arrays" of oligonucleotides and proteins (as outlined in "Multianalyte Molecular Analysis Using Application-Specific Random Particle Arrays," U.S. application Ser. No. 10/204,799, filed on Aug. 23, 2002; WO 01/98765), arrays of oligonucleotides or proteins arrays can be formed by displaying these capture moieties on chemically encoded microparticles ("beads") which are then assembled into planar arrays composed of such encoded functionalized carriers. See U.S. patent application Ser. No. 10/271,602 "Multiplexed Analysis of Polymorphic Loci by Concurrent Interrogation and Enzyme-Mediated Detection," filed Oct. 15, 2002, and Ser. No. 10/204, 799 supra.

Microparticle arrays displaying oligonucleotides or proteins of interest can be assembled by light-controlled electrokinetic assembly near semiconductor surfaces (see, e.g., U.S. Pat. Nos. 6,468,811; 6,514,771; 6,251,691) or by a direct disposition assembly method (previously described in Provisional Application Ser. No. 60/343,621, filed Dec. 28, 2001 and in U.S. application Ser. No. 10/192,352, filed Jul. 9, 2002).

To perform nucleic acid or protein analysis, such encoded carrier arrays are placed in contact with samples anticipated to contain target polynucleotides or protein ligands of interest. Capture of target or ligand to particular capture agents displayed on carriers of corresponding type as identified by a color code produces, either directly or indirectly by way of subsequent decoration, in accordance with one of several known methods, an optical signature such as a fluorescence signal. The identity of capture agents including probes or protein receptors (referred to herein sometimes also collectively as "receptors") generating a positive assay signal can be determined by decoding carriers within the array.

These microparticle arrays can exhibit a number of spectrally distinguishable types of beads within an area small enough to be viewed in a microscope field. It is possible to achieve a high rate of image acquisition because the arrays obviate the need for confocal laser scanning (as used with spotted or in-situ synthesized arrays) and instead permit the use of direct ("snapshot") multicolor imaging of the entire array under a microscope. If the system could be automated further, such that, for example, the microscope is automatically repositioned to optimally capture images from multiple arrays present on a multichip carrier and to positions optimizing decoding of the array, this would facilitate unattended acquisition of large data lots from multiplexed assays.

In one format using microbead arrays, the encoding capacity of a chip (which includes several distinct subarrays) can be increased even where using the same set of color codes for the beads in each subarray. When subarrays are spatially distinct, the encoding capacity becomes the product of the number of bead colors and the number of subarrays.

In order to match the rates of data acquisition enabled by direct imaging, rapid and robust methods of image processing and analysis are required to extract quantitative data and to produce encrypted and compact representations suitable for rapid transmission, particularly where there is off-site analysis and data storage. Transmission of data should be secure, and should be accessible only by authorized parties, including the patient but, because of privacy concerns, not to others.

SUMMARY

Disclosed are methods of increasing the confidence of the analysis, and for rapid and automated decoding of encoded arrays used in assays, assay data recorded in the form of images generated from arrays of ligand-receptor interactions; and more particularly, where different receptors are associated with different encoded microparticles ("beads"), and results are determined upon decoding of the arrays. Also disclosed are methods for transmitting and archiving data from such assay arrays in a manner such that access is limited to authorized persons, and such that the chance of assigning one patient's results to another are minimized. These methods are particularly useful where assays are performed at decentralized user ("client") sites, because the methods permit secure exchange of data between the client and a central facility ("information keeper"), where the data can be centrally decoded and analyzed so as to provide greater reliability, and then archived in a restricted manner where only authorized users have access.

In a centralized regime, patient samples, collected in the field, are sent for analysis to a central location, where they are assayed. Results are provided to authorized users by remote transmission. Users, while relieved of any responsibility relating to assay completion and data analysis, are faced with the loss of control over the assay implementation and analysis and may face the inconvenience of significant delay. Non-standard assays may be unavailable or prohibitively expensive. In addition, this service ordinarily will not be suitable for perishable samples, or large to collections of samples, such as those created in a pharmaceutical research laboratory.

In a decentralized paradigm, analytical instrumentation, such as microplate readers complete with all requisite software, are distributed to users who perform assays, record results, and may also perform subsequent data analysis. Alternatively, assay results may be transmitted to a central facility for decoding, analysis, processing and archiving, and such centralized procedures may provide greater reliability.

The analysis server model (useful, inter alia, for molecular diagnostics), as disclosed herein, expands upon these paradigms by combining decentralization of assay performance with centralized data analysis. That is, while assay performance and data generation are at user facilities, critical aspects of subsequent data analysis and related services may be performed in a centralized location which is accessible to authorized users in a two-way mode of communication via public or private computer networks. The analysis server model can be applied to assays performed in a highly parallel array format requiring only a simple imaging instrument, such as a microscope, to record complex assay data, but requiring advanced methods of analysis and mathematical modeling to reliably process and analyze assay data. Images, recorded at a user location, are uploaded to a centralized location where such analysis are performed, results being made available to authorized users in real time.

The methods and processes are further explained below with reference to the drawings.

BRIEF DESCRIPTION OF THE DRAWINGS

FIG. 9A shows a grid (with extra rows and columns) in unshifted position (0,0).

FIG. 9B shows the grid of FIG. 9A and in a configuration shifted to position (1,1).

FIG. 9C illustrates the seven possible shifting positions for the grid of 9A and 9B.

FIG. 13 shows a READER Graphical User Interface (GUI) illustrating steps in the course of processing a assay image.

FIG. 14 illustrates a decoded assay data record in histogram form.

DETAILED DESCRIPTION

Figure 1:
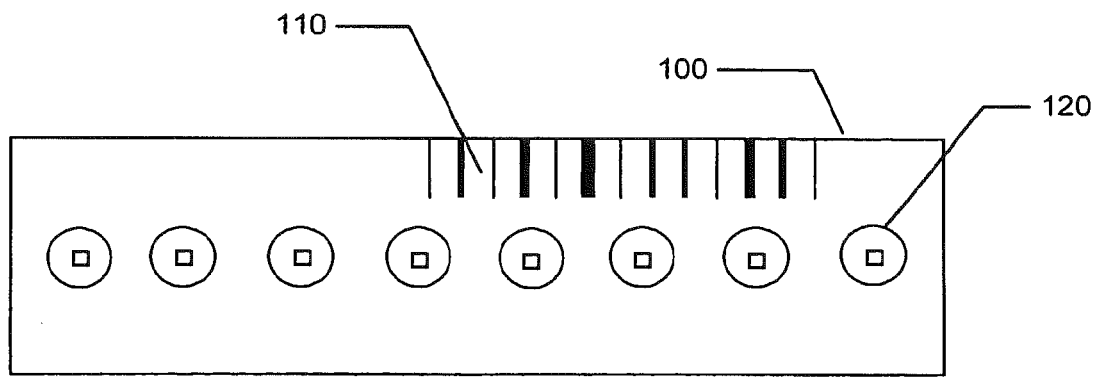
FIG. 1 displays a 1×8 multichip carrier, where chips with encoded arrays on a surface are housed in the carrier's wells.

FIG. 1 depicts a multichip carrier (100) displaying a barcode (110) along with a set of 2×2 chips (120) in each of eight positions, each such chip comprising one or more random array(s) of encoded microparticles (130). The decoding of the microparticles 130 and analysis and transmission of the data can be performed in accordance with the methods described herein. Each of the 2×2 chip subarrays (i.e., four chips) correspond with one individual patient sample. Thus, given a set of 128 distinguishable colors for the beads in the array, this can produce an array complexity of 4×128=512 for each individual. The 1×8 sample format shown in FIG. 1 with a center-to-center distance of 9 mm matches the standard 8×12 microwell format and is readily scaled to n×8 for high-throughput sample handling (as described further in U.S. patent application Ser. No. 10/192,352).

Figure 2:
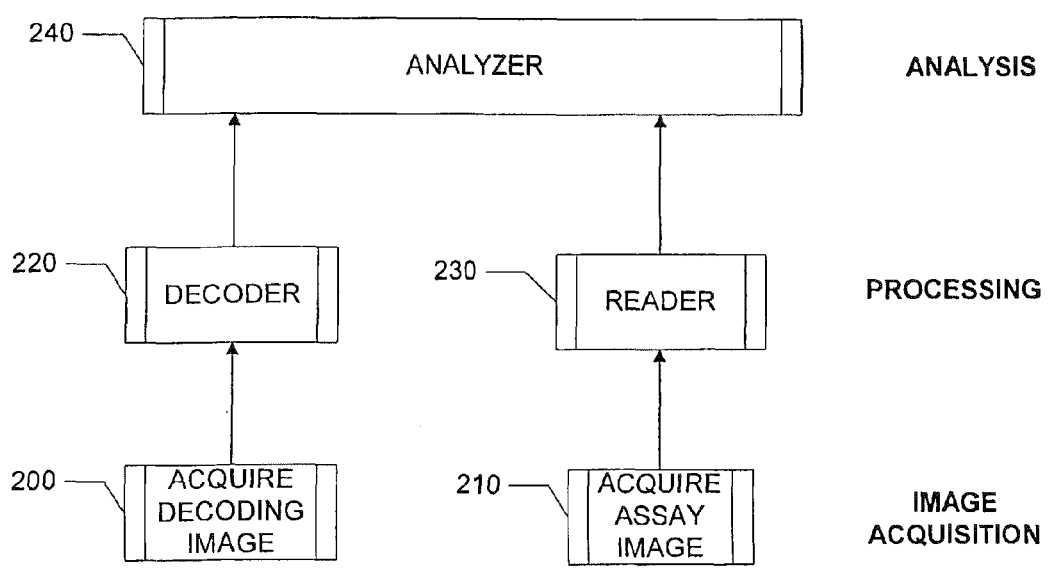
FIG. 2 is a flowchart of an imaging system, including image acquisition, a decoder and a reader for image processing, and an analyzer for data analysis.

As illustrated in FIG. 2, the imaging system comprises hardware for acquiring a decoding image (200), means for acquiring an assay image (210), a decoder (220), a reader (230), and an analyzer (240). Acquiring and recording a decoding image or an assay image can be accomplished using the system shown in FIG. 4.

Molecular interaction analysis on a random array of encoded microparticles or beads, where each subpopulation of such encoded beads displays a unique receptor molecule, for example, an oligonucleotide, or protein molecule, can be performed using these systems. Each such receptor is designed so as to be able to form a molecular complex with a cognate target analyte or ligand, the formation of a complex resulting in an, optical signature (for example, the ligand can be fluorescently labeled and thus detectable following complex formation) that is detected by acquiring and analyzing images of the array. Assay results take the form of an image comprising a set of intensities, each of which is uniquely associated with one receptor-ligand interaction in the array. Such assays are well-suited for DNA and protein analysis performed in a multiplexed or parallel mode using an array format, including applications such as genetic expression profiling, polymorphism and mutation analysis, protein-protein analysis including antibody-antigen interaction analysis, organic compound-receptor interactions, and further including all those disclosed in PCT/US01/20179, U.S. Pat. Nos. 6,251,691; 6,387,707 and U.S. patent application Ser. No. 10/271,602, all of which are incorporated herein by reference.

The decoding of encoded arrays and the analysis, interpretation or storage of assay results requiring access to methods and algorithms or access to databases which are not available at the location housing the analytical instrumentation, but are instead available at a remote location, is addressed herein. Special consideration is given to situations in which these operations, or parts thereof such as the collection and preparation of a sample, the actual assay or assays of interest and additional operations such as interpretation or consultation are performed in separate locations. In one embodiment, the methods and apparatus described herein permit complex multianalyte analysis to be performed in locations visited by a patient whose sample is collected and analyzed on site, while providing transaction protocols to perform data analysis and optional additional services, such as data interpretation and archiving to be performed off-site. The methods herein permit the secure exchange of information recorded on site and analyzed at the site of an application service provider.

Accordingly, the systems and methods provided herein for the analysis of clinical samples or other analytes provide for communication among three (or optionally more) participants, including: (i) the sample originator, for example a patient seeking clinical diagnosis or a biomedical research laboratory seeking analytical services; (ii) the analysis provider (which may or may not also be the tester performing the assay); and (iii) the tester, which performs the assay but is generally provided minimal information about assay outcomes, decoding, or sample origination; and (iv) an optional intermediary, for example a sample collector and/or processor or communicator of results, such as a counselor.

These methods allow the rapid assaying and analysis of customized random encoded bead arrays, where a multiplexed assays are performed on patient samples, and multiple assays may be conducted. Suitable panels may include, for example, a tumor marker panel including antigens such as PSA and other suitable tumor markers, an allergy panel, a pregnancy panel comprising tests for human chorionic gonadotropin, hepatitis B surface antigen, rubella virus, alpha fetoprotein, 3' estradiol and other substances of interest for monitoring a pregnant individual; a hormone panel, an autoimmune disease panel including tests for rheumatoid factors and panel reactive antibodies and other markers associated with autoimmune disorders, a panel of blood-borne viruses and a therapeutic drug panel comprising tests for Cyclosporin, Digoxin and other therapeutic drugs of interest.

In addition, such panels also may include, for example, oligonucleotide probes designed for nucleic acid analysis including analysis of cDNA panels for gene expression profiling, oligonucleotide probe panels designed for the multiplexed analysis of mutations causing genetic diseases such as cystic fibrosis, Tay-Sachs disease, Ashkenazi Jewish diseases including Gaucher disease and others, the analysis of polymorphisms such as those in the Human Leukocyte Antigen complex which determine the degree of compatibility between donor and recipient in transplantation of bone marrow or solid organs, a blood antigen panel for blood typing, the analysis of chromosomal aberrations such as those underlying Down Syndrome and others surveyed in prenatal screening or certain blood-borne cancers such as certain leukemias. The multiplexed nucleic acid analysis involved in assaying of these panels can be performed using either hybridization-mediated detection or hybridization-mediated elongation-mediated detection, as described in U.S. patent application Ser. No. 10/271,602, entitled: "Multiplexed Analysis of Polymorphic Loci by Concurrent Interrogation and Enzyme-Mediated Detection" filed Oct. 15, 2002.

In either hybridization-mediated detection or hybridization-mediated elongation-mediated detection, an association of polynucleotide in the sample with a probe oligonucleotide on a bead results in an assay signal in the form of an optical signature. For example, in the READ™ format, each encoded bead within the array (where each bead has multiple probes attached thereto) may produce one or more of such optical signatures which are able to be recorded by the systems of the invention. The optical signature can be a fluorescence signature. Optical signatures of interest include, without limitation, luminescence including bioluminescence, chemiluminescencve and electrochemiluminescence. Direct visual signatures resulting, for example, from the transformation of the assay locus, for example, by agglutination of multiple beads, or the attachment of marker particles to assay loci, can also be recorded and analyzed using the methods set forth herein.

I. Automated High-Throughput Array Imaging for Molecular Interaction Analysis

I.1 Assay and Decoding Data Records

Figure 3:
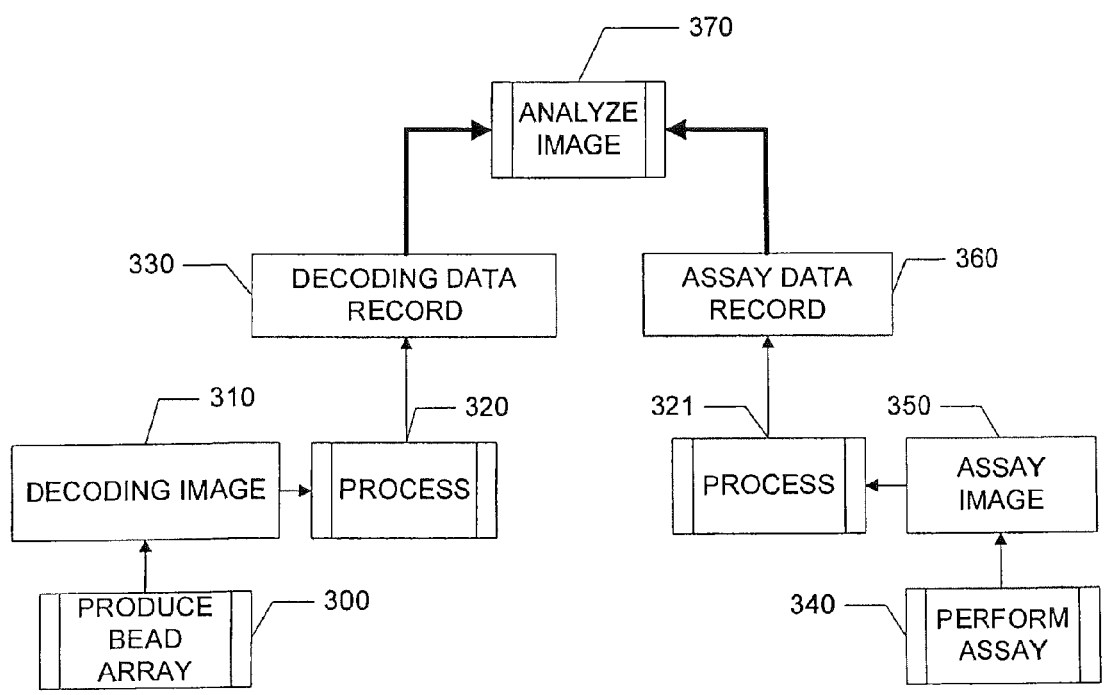
FIG. 3 is a flowchart illustrating an exemplary system where assay data can be decoded and centrally analyzed.

FIG. 3 is an illustration of the methods to conduct the analysis of analytes using bead arrays assembled on substrates, according to the READ process of multiplexed analysis. The method of FIG. 3 involves producing a bead array (300), obtaining a decoding image (310), processing the decoding image using a decoder (320), and obtaining a decoding data record (330). In parallel, an assay is performed using the bead array (340) to obtain an assay image (350), where the assay image is processed using a reader (321) and the assay data is recorded (360). The decoding data and assay data are then combined and the image is analyzed (370). The decoding image may represent a combination of several distinct images recorded in separate spectral bands or color channels, where the encoding is with chemically and/or physically distinguishable characteristics that uniquely identify the binding agent displayed on the bead surface. For example, when the uniquely distinguishable characteristic is color, a "decoding image" of the bead array (where the bead are immobilized on the substrate) is recorded to reference the color code of constituent beads, where the color code uniquely corresponds to the chemical identity of the binding agents displayed on each individual bead's surface.

Referring to FIG. 3, the decoding image (310) may be generated following completion of array assembly by the array manufacturer at the manufacturing site or it may be generated by the user of the array in connection with the completion of a bioassay or other chemical test, either prior to, or subsequent to completion of the assay or test at the test site. The decoding image (310) becomes part of the decoding data record (330), which also contains a variety of identifiers for reagent, microparticle and substrate batch and lot numbers. The decoding image (310) can be generated following array assembly at the manufacturing site and processed to create a decoding data record (330) which is stored in a database on a central server. Access to the decoding data record, or parts thereof, can be accessible in the form of a copy the record, for example, of copies on a recording medium such as a CD that is distributed along with arrays and multichip carriers or cartridges. Alternatively, access to the decoding data record, or parts thereof, is made accessible in the form of authenticated database accessible only to authorized users as disclosed herein.

Following completion of an assay (340) at a user site, the assay image is recorded (350) and an Assay Data Record (360) is created which serves to record the optical signature(s) indicating the binding of ligand molecules to immobilized receptors. For example, when fluorescence is selected to provide the optical signature of interest, the fluorescence intensity recorded from each position within the array indicates the amount of complex formed in that location by receptor and ligand binding or hybridization. Multiple modes of generating such optical signatures include the direct or indirect labeling of target analytes (for example, by using fluorescent primers to conduct PCR of genomic regions to be assayed) or the introduction of fluorescence by way of probe elongation using labeled nucleotides. See, e.g., U.S. patent application Ser. No. 10/271,602 "Multiplexed Analysis of Polymorphic Loci by Concurrent Interrogation and Enzyme-Mediated Detection." The assay image forms the assay data record.

As described herein below, the methods herein can be used for processing decoding and assay images, for extracting representations suitable for rapid transmission and for rapidly and reliably combining decoding and assay image signatures so as to associate assay results recorded from specific array locations with corresponding chemically encoded probe identities.

Assembly of Random Encoded Bead Arrays. Random encoded arrays may be assembled by the methods described in U.S. Pat. No. 6,251,691, or in U.S. patent application Ser. No. 10/192,352, entitled "Arrays of Microparticles and Methods of Preparation Thereof," incorporated herein by reference in its entirety. These methods combine separate batch processes that respectively serve to produce application-specific substrates (e.g., chips at the wafer scale) and encoded bead libraries whose constituent beads are functionalized (e.g., at the scale of $\sim 10^8$ beads/100 ul of suspension) to display receptors, such as nucleic acids and proteins of interest. Beads assembled in an array may be immobilized by physical or chemical means to produce fixed random encoded arrays.

In addition, the methods described in U.S. Pat. No. 6,251,691 may be used to form multiple bead arrays. Alternatively, multiple bead arrays can be formed simultaneously in discrete fluid compartments maintained on the same chip. The integration of array assembly with microfluidics produces a self-contained, miniaturized, optically programmable platform for parallel protein and DNA analysis. Once formed, these multiple bead arrays may be used for concurrent processing of multiple samples.

Spatial encoding of multiple arrays also can be accomplished by assembling planar bead arrays in a desired location, using discrete fluid compartments or the assembly methods described in U.S. Pat. No. 6,251,691. Alternatively, spatial encoding can be accomplished by assembling separate chips, each carrying at least one random encoded array drawn from a specific pool, into a designated configuration of multiple chips.

Chemical Encoding and Functionalization of Beads. Chemical encoding may be accomplished by staining beads with sets of optically distinguishable tags, such as those containing one or more fluorophore dyes spectrally distinguishable by excitation wavelength, emission wavelength, excited-state lifetime or emission intensity. Two-color and three-color combinations, where the latter may be constructed as "stacked" two-color combinations, are decoded as described herein.

The optically distinguishable tags may be used to stain beads in specified ratios, as disclosed, for example, in Fulwyler, U.S. Pat. No. 4,717,655, which is incorporated herein by reference in its entirety. Staining may also be accomplished by swelling of particles in accordance with methods known to those skilled in the art (see, e.g., Molday, Dreyer, Rembaum & Yen, J. Mol Biol 64, 75-88 (1975); L. Bangs, "Uniform latex Particles, Seragen Diagnostics, 1984). Beads can be encoded' by swelling and bulk staining with two or more colors, each individually at separate intensity levels, and mixed in separate nominal molar ratios in accordance with methods known to the art. See also U.S. patent application Ser. No. 10/348,165, entitled: Method of Controlling Solute Loading of Polymer Microparticles; filed Jan. 21, 2003. Combinatorial color codes for exterior and interior surfaces is disclosed PCT/US98/10719, which is incorporated herein by reference.

Beads to be used in the bead arrays of the invention for biomolecular analysis are functionalized by a binding agent molecule attached thereto, where the molecule may be, for example, DNA (oligonucleotides) or RNA, fragments, peptides or proteins, aptamers and small organic molecules attached in accordance with processes known in the art, e.g., with one of several coupling reactions of the known art (G. T. Hermanson, *Bioconjugate Techniques* (Academic Press, 1996); L. Ilium, P. D. E. Jones, *Methods in Enzymology* 112, 67-84 (1985)). The binding agent molecule may be covalently attached to the bead. Beads may be stored in a buffered bulk suspension until needed.

Functionalization typically may be performed, for example, with a one-step or two-step reaction which may be performed in parallel using standard liquid handling robotics and a 96-well format to covalently attach any of a number of desirable functionalities to designated beads. Beads of core-shell architecture may be used (as described in U.S. Provisional Application entitled: "Ionic Gel-Shell Beads with Adsorbed or Bound Biomolecules," filed Oct. 28, 2003, and applications claiming priority thereto) where the shell is a polymeric layer. Samples may be drawn along the way for automated QC measurements. Each batch of beads preferably has enough members such that chip-to-chip variations with different beads on chips are minimized.

Beads may be subjected to quality control (QC) steps prior to array assembly, for example, the determination of morphological and electrical characteristics, the latter including surface ("zeta") potential and surface conductivity. In addition, assays may be performed on beads in suspension before they are introduced to the substrate, to optimize assay conditions, for example, to maximize assay sensitivity and specificity and to minimize bead-to-bead variations. QC steps for substrates may include optical inspection, ellipsometry and electrical transport measurements. Substrates. Substrates, e.g., silicon wafers and chips, are used which may be patterned by invoking standard methods of semiconductor processing, for example to it) implement interfacial patterning methods of LEAPS by, e.g., patterned growth of oxide or other dielectric materials to create a desired configuration of impedance gradients in the presence of an applied AC electric field. See U.S. Pat. No. 6,251,691. Patterns may be designed so as to produce a desired configuration of AC field-induced fluid flow and corresponding particle transport, or to trap particles in wells, as described in US Provisional Application entitled: Immobilization of Bead-displayed Ligands on Substrate Surfaces," filed Jun. 12, 2003, Ser. No. 60/478,011.

In addition, substrates may be compartmentalized by depositing a thin film of a UV-patternable, optically transparent polymer to affix to the substrate a desired layout of fluidic conduits and compartments to confine fluid in one or several discrete compartments, thereby accommodating multiple samples on a given substrate. Other substrates such as patternable or machinable ceramics also are suitable.

Customization by Pooling. Bead-displayed probes of interest can be selected from a library of beads and pooled prior to array assembly. That is, customization of assay composition is achieved by selecting aliquots of designated encoded beads from individual reservoirs in accordance with a specified array composition. Aliquots of pooled suspension are dispensed onto a selected substrate (e.g., a chip). The aliquots may be mixed or may be separated to form a multiplicity of planar random subarrays of encoded beads, each subarray representing beads drawn from a distinct pool. The array may be laid out in a manner such that aliquot positions in the array correspond to the identity of each aliquot of the pooled bead population.

Array Analysis. The binding interaction between the receptor (which may be an oligonucleotide) displayed on color-encoded functionalized beads and a ligand (or "analyte") may be analyzed after a random encoded bead array is assembled in a designated location on the substrate or chip. For example, bead arrays may be formed after completion of the assay, subsequent to which an assay image and a decoding image may be taken of the array.

Immobilization Microparticle arrays may be immobilized by mechanical, physical or chemical anchoring as described in PCT/US01/20179 (counterpart of U.S. patent application Ser. No. 10/192,352), including by trapping particles in wells, as described in US Provisional Application entitled: Immobilization of Bead-displayed Ligands on Substrate Surfaces," filed Jun. 12, 2003, Ser. No. 60/478,011.

In certain embodiments, bead arrays may be immobilized by physical adsorption mediated by application of a DC voltage, set to typically <5V (for beads in the range of 2-6 γm, a gap size of 100-150 γm, and a silicon oxide layer of ~100 Angstrom thickness). Application of such a DC voltage for <30 s in "reverse bias". configuration—so that an n-doped silicon substrate would form the anode—causes bead arrays to be permanently immobilized. See U.S. Pat. No. 6,251,691.

In certain embodiments, the particle arrays may be immobilized by chemical means, e.g., by forming a composite gel-particle film. In one exemplary method for forming such gel-composite particle films, a suspension of microparticles is provided which also contain all ingredients for subsequent in-situ gel formation, namely monomer, crosslinker and initiator. The particles may be assembled into a planar assembly on a substrate by application of the LEAPS™ process, as described in U.S. Pat. No. 6,251,691. Following array assembly, and in the presence of the applied AC voltage, polymerization of the fluid phase is triggered by thermally heating the cell ~40-45° C. using an IR lamp or photometrically using a mercury lamp source, to effectively entrap the particle array within a gel. Gels may be composed of a mixture of acrylamide and bisacrylamide of varying monomer concentrations, from about 20% to 5% (acrylamide: bisacrylamide=37.5:1, molar ratio), or, in the alternative, any other low viscosity water soluble monomer or monomer mixture may be used as well. In one example, thermal hydrogels are formed using azodiisobutyramidine dihydrochloride as a thermal initiator at a low concentration ensuring that the overall ionic strength of the polymerization mixture falls in the range of ~0.1 mM to 1.0 mM. The initiator used for the UV polymerization is Irgacure 2959® (2-Hydroxy-4'-hydroxyethoxy-2-methylpropiophenone, Ciba Geigy, Tarrytown, NY). The initiator is added to the monomer to give a 1.5% by weight solution. The methods described in U.S. patent application Ser. No. 10/034,727 are incorporated herein by reference.

In certain embodiments, the particle arrays may be immobilized by mechanical means, for example, such arrays may be placed into an array of recesses may be produced by standard semiconductor processing methods in the low impedance regions of the silicon substrate. The particle arrays may moved into the recesses by, e.g., utilizing LEAPS™-mediated hydrodynamic and ponderomotive forces to transport and accumulate particles in proximity to the recesses. The A.C. field is then switched off and particles are trapped into the recesses and mechanically confined. Excess beads are removed leaving behind a geometrically ordered random bead array on the substrate surface.

Carriers and Cartridges. Substrates (e.g., chips) with immobilized bead arrays may be placed in distinct enclosed compartments, and samples and reagents may be transported in and out of the compartments by means of fluidic interconnection. On-chip immunoassays, including those for various cytokines, e.g., interleukin (IL-6) may be performed in this format. In such immunoassays, samples are allowed to react with beads immobilized on the chip and adsorption of targets in the samples by the receptors on the beads may be detected by binding of fluorescently labeled secondary antibodies.

Random Encoded Array Detection. Once the functionalized and encoded beads are prepared, and assembled on the substrate, a binding assay may be performed. The array can function as a two-dimensional affinity matrix which displays receptors or binding agents (e.g., oligonucleotides, cDNA, aptamers, antibodies or other proteins) to capture analytes or ligands (oligonucleotides, antibodies, proteins or other cognate ligands) from a solution or suspension that is brought in contact with the array. The bead array platform may be used to perform multiplexed molecular analysis, such as, e.g., genotyping, gene expression profiling, profiling of circulation protein levels and multiplexed kinetic studies, and may be used for the implementation of random encoded array detection (READ™), including analysis based on image acquisition, processing and analysis.

I.2 Multicolor Image Acquisition Using an Automated Array Imaging System

Multicolor images can be used to encode and display information recorded in two or more color channels. The construction of multicolor images can be accomplished by merging two or more images recorded in separate spectral bands and distinguished by selection of suitable color filter combinations, as is well-known in the art.

The READ™ format provides for multicolor images before and after the assay, referred to respectively as a decoding image and an assay image. The decoding image serves to record the location of particular identified solid phase carriers—and hence the identity of receptors displayed on such carriers—based on their color-encoding in an array. These solid phase carriers may be color encoded using, for example, combinations of two or more fluorescent dyes. The assay image reflects the optical signatures induced by association of target analytes with carrier-displayed receptors. In one example, useful in gene expression profiling, signal produced on an array by the hybridization of cDNA or RNA produced from a tissue sample of interest and labeled with fluorescent dye (e.g., Cy5) may be compared with the signal produced from a known quantity or concentration of cDNA or RNA produced from a reference sample and labeled with a fluorescent dye, (e.g., Cy3 or Cy5). The comparison of signal from the tissue sample and the reference sample indicates the level of gene expression. An analogous format may be used in molecular cytogenetics applications. Protein-protein interactions can also be monitored with this format, where the protein in the sample is labeled following its association with the bead-bound protein in the array, for example, by using a labeled antibody which targets the protein.

Multicolor images obtained from monitoring of random encoded arrays can be recorded automatically. The arrays can be formed on chips, and multiple chips can be placed on a carrier, such as that shown in FIG. 1. However, alternative modes of presenting and arranging random encoded arrays are possible. For example, samples also may be mounted in flow cells or cartridges permitting fluidic operation so as to inject samples, reagents and buffers, permitting imaging of probe array by way of standard microscope optics.

The components and subsystems of an exemplary image acquisition system may include the following:

Input/Output File System: images are handled in TIFF format, other files are handled in XML (eXtensible Markup Language) format; an XML output file records the settings of parameter such as image acquisition integration time, filter selection System Status: illumination source (ON/OFF), stage target position Mechanical Subsystems: xy translator, z actuator, filter wheel, ND filters Barcode Reader Image Acquisition and Storage Control Software Graphical User Interface (GUI)

Autocenter Function (implemented by Software)

Autofocus Function (implemented by Software)

Figure 4:
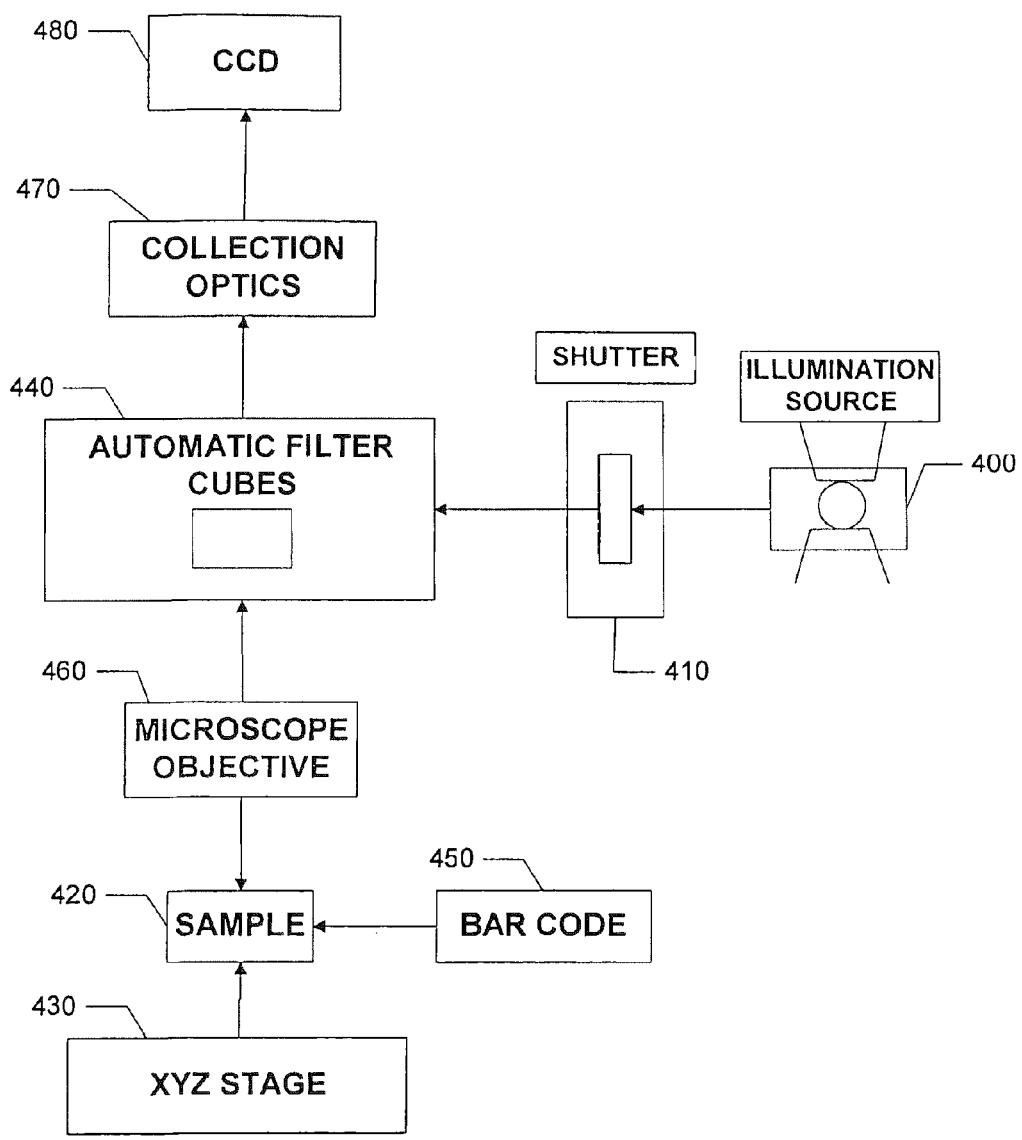
FIG. 4 is a flowchart illustrating viewing a multiplexed assay and recording of the assay image.

Hardware. FIG. 4 shows a microscope, for use in an imaging system, providing transmission or reflection geometry and multiple methods of generating optical contrast. In one embodiment, reflection geometry is chosen to record "brightfield" (e.g., an image not recorded under fluorescence optical contrast imaging conditions, including an image recorded under white light illumination) as well as multicolor fluorescence images in a fully automated manner.

Other components and subsystems of an imaging system are set forth below.

Illumination Source. Depending on the application of interest, any suitable illumination source (400) can be used, including a laser, or a standard microscope illumination sources including tungsten halogen, mercury and xenon. In one embodiment, a xenon light source is used for multi-fluorescence imaging. A mechanical shutter (410) controls "Light-ON" and "Light-OFF" functions.

Mechanical Subsystems. Certain subsystems can be used to control precision positioning of the sample (420), selection of image mode, namely brightfield or (epi)fluorescence (using different filters), and spectral filter selection. The positioning of the sample involves horizontal and vertical sample positioning, deploying a computer-controlled xy-translator (part of the xyz stage (430)), which can be under the control of a manual "joystick" positioning function or an automated autocentering function, and a z-actuator connected to a vertical motion of the sample under control of an autofocusing function which may be computer-controlled. Fluorescence filter combinations can be selected automatically using a computer controlled carousel housing filter cubes (440).

Barcode Scanner. A handheld barcode scanner (450) can be used to scan an identifying barcode affixed to each multi-chip carrier or other sample carrier or cartridge. The barcode can identify, for example, the composition of beads associated with the carrier, the origin of the carrier (i.e., the batch it is derived from) or other information.

Optical Subsystem—A combination of microscope objective (460) and collection optics (470) in standard configuration, or in Koehler configuration, is used for illumination as well as collection and image formation.

CCD Camera. A CCD camera (480), preferably with C-mount, is attached to the microscope to record images.

Control Software. The fully automated operation of the array imaging system is enabled by control software (also referred to herein as the Array Imaging System—Operation Software ("AIS-OS")) comprising a Graphical User Interface (GUI) as well as control algorithms implementing autocentering and autofocus functions, as set forth below.

Operation of Array Imaging System. Bead arrays mounted in a multichip carrier or cartridge are placed on the translation stage of the Array Imaging System ("AIS") and multicolor images (both decoding and assay images) are recorded. Table I below shows the pseudocode for the translation/decoding operation of the Array Imaging System.

TABLE I

```
IF (record Decoding Image mode) {
   LoadFile (Production Data Record); /** Load or Create **/
   ScanBarCode (Carrier ID);
   WriteInfo (Carrier ID, Number of BeadChips on Carrier,
   ProductionDataRecord);
};
ELSE IF (record Assay Image mode) {
   ScanBarCode(Carrier ID);
   ReadInfo (Production Data Record, CarrierID, Number of BeadChips on
   Carrier);
          /** The Production Data Record is accessible as an
          XML file in the folder set up by the AIS for each
          sample **/
   ConstructFileName (AssayDataRecord)     /** to match Production
   Data Record **/
   WriteInfo(Assay Data Record, CarrierID, Number of BeadChips on
   Carrier);
          /** Production Data Record and Assay Data Record
          are maintained on an SQL database server accessible
          to authenticated users **/
};
index = 0;
WHILE( index < Number of BeadChips on Carrier)
{
   IF (record Assay Image mode) {
      ReadTargetPosition(Production Data Record, BeadChipID, X, Y, Z);
   };
   MoveXYTranslator ( X, Y );MoveZTranslator (Z);
   Z = AutoFocus(Z);              /** perform autofous operation **/
   AutoCenter(X, Y);    /** In record Decoding Image mode,
          operator sets first center position **/
   Z = AutoFocus(Z);              /** repeat autofocus **/
   IF (record Decoding Image mode) {
      WriteTargetPosition(Production Data Record, BeadChipID, X, Y, Z);
   };
   FOR (each desired ColorChannel) {
      SetFilter (ColorChannel);
      AcquireImage ( );          /** See details below **/
      WriteImageFile(CarrierID, BeadChipID, ColorChannel, ImgFile);
      IF (record Decoding Image mode) {
         UpdateProductionDataRecord(CarrierID, BeadchipID,
         ImgFileName);
      };
      ELSE IF (record Assay Image mode) {
         UpdateAssayDataRecord(CarrierID, BeadChipID,
         ImgFileName);
      };
   };
   index++ ;
};
```

Autocentering. The autocentering function, using a given input image, positions the XY translation stage so as to place each selected array into the center of the imaging system's field view by determining that the image in the viewing field is, in fact, a rectangle with the correct number of sides and right angle corners. This is accomplished by performing the steps in Table II, which shows the pseudocode for the autocentering operation:

TABLE II

```
OpenImg(InputImg, OpenedImg);     /** apply sequence of morphological
erosion and dilation operations to eliminate internal structure of the image
showing particle array **/
Binarize(OpenedImg,BinImg);              /** apply optimal
thresholding algorithm **/.
CloseImg (BinImg, ClosedImg);            /** apply sequence
of morphological dilation and erosion operations **/
AnalyzeConnectivity (ClosedImg, ConComp);  /** find connected
components in closed image **/
Filter (ConComp, FilteredConComp);       /** filter out all
"non-box-like" regions; a "box-like" region is defined as a region whose
area is close to the area of its "bounding box" **/
Center = FindMaxConComp(FilteredConComp);  /** find largest
connected component that is smaller than 70% of the image size and
find its centroid **/
MoveXYTranslator ( Center.X, Center.Y );  /** position stage **/
```

Only when a new multichip carrier ("MCC") is first inspected and decoded, does the positioning of the very first array on the MCC require interactive operation. This initial positioning step is performed as a part of array assembly or subsequent quality control. All subsequent positioning may be automatic. The full processing-positioning followed by acquiring of multiple images and displaying a rendering of a multicolor image typically requires only a few minutes.

Autofocusing. The autofocusing function positions the Z actuator so as to bring the image in focus and place each selected array into the center of the imaging system's field view. An algorithm which uses a local contrast function to determine optimal focus can be used. This local contrast is determined as follows using a fast computation: evaluate, for each pixel, a quantity $\Delta_{max}$, defined as the largest absolute value of the difference in intensity between that pixel and its four horizontal and vertical neighbors; next, sum the $\Delta_{max}$ over a designated portion of the image: this serves to speed up the operation. The Z-position of maximal contrast is located. The autofocus function should help ensure vertical positioning to within one micron or less.

I.3 Performing Multi-Analyte Molecular Analysis

Figure 5:
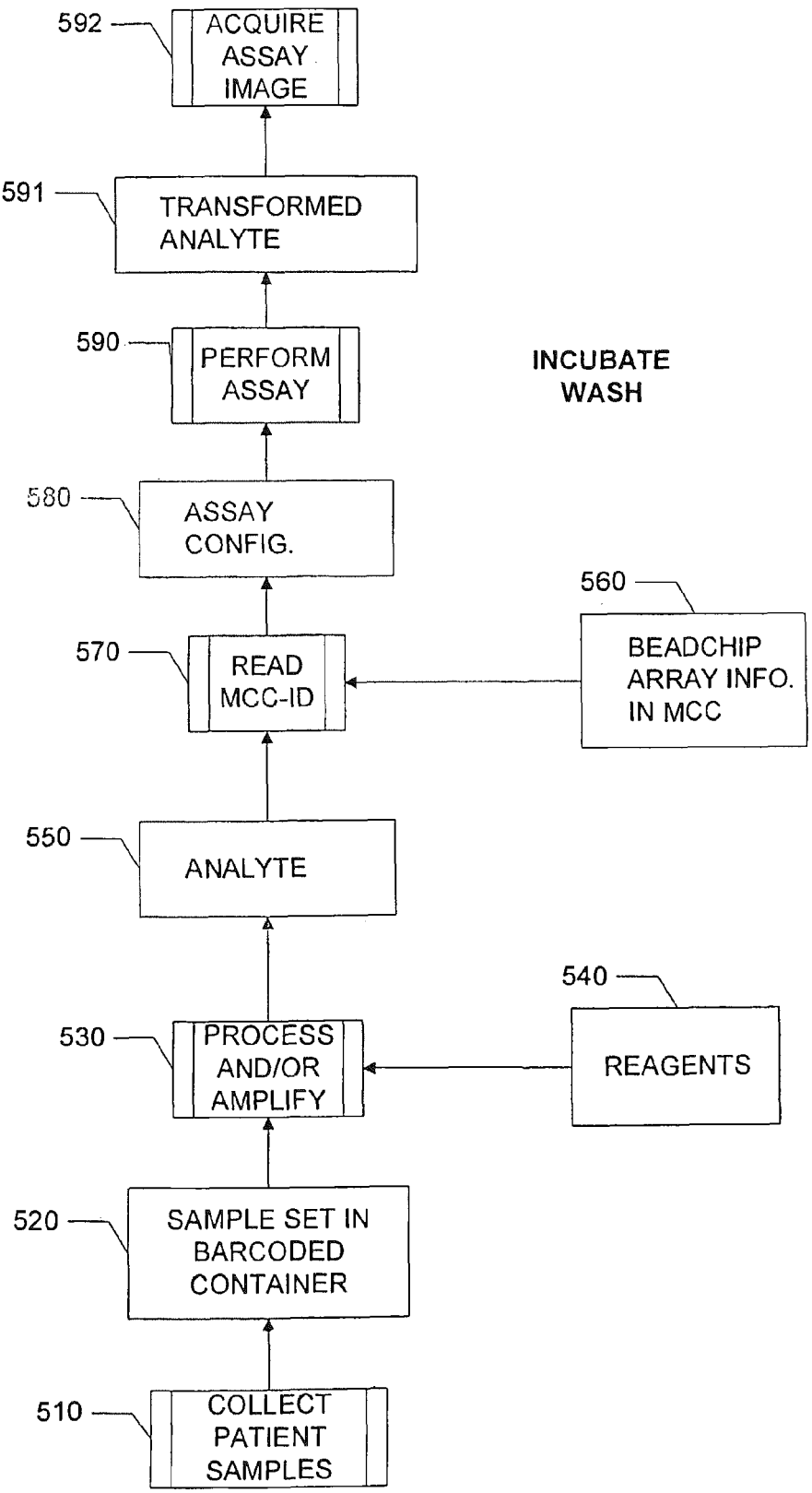
FIG. 5 is a flowchart depicting sample collection, performing of assays and acquisition of an assay image.

The process of performing multianalyte molecular analysis using the system herein would, in an exemplary embodiment, involve the concatenation of the previously described operations as follows (FIG. 5):

Collect patient sample (510)

Transfer to sample container, preferably a barcoded sample container (520)

Process sample (530) using requisite reagents (540) to produce analyte (550)

Select multichip carrier (MCC), obtain MCC information (560)

(580), for example, positions of beadchips arranged on MCC;

Perform assay (590) to produce transformed analyte (591) to be analyzed

Mount MCC in array imaging system and read MCC barcode (570) to obtain assay configuration Acquire assay image(s)(592)

Submit assay image data for processing and analysis, details of which are described below.

II Image Processing and Analysis

Processing, analyzing, transmitting and storing images as set forth herein can be implemented in Visual C++ (Microsoft) using a graphical user interface software package including .exe files implementing the pseudocodes and flow diagram steps described herein including, for example, the analysis, processing and decoding steps described herein.

Figure 6:
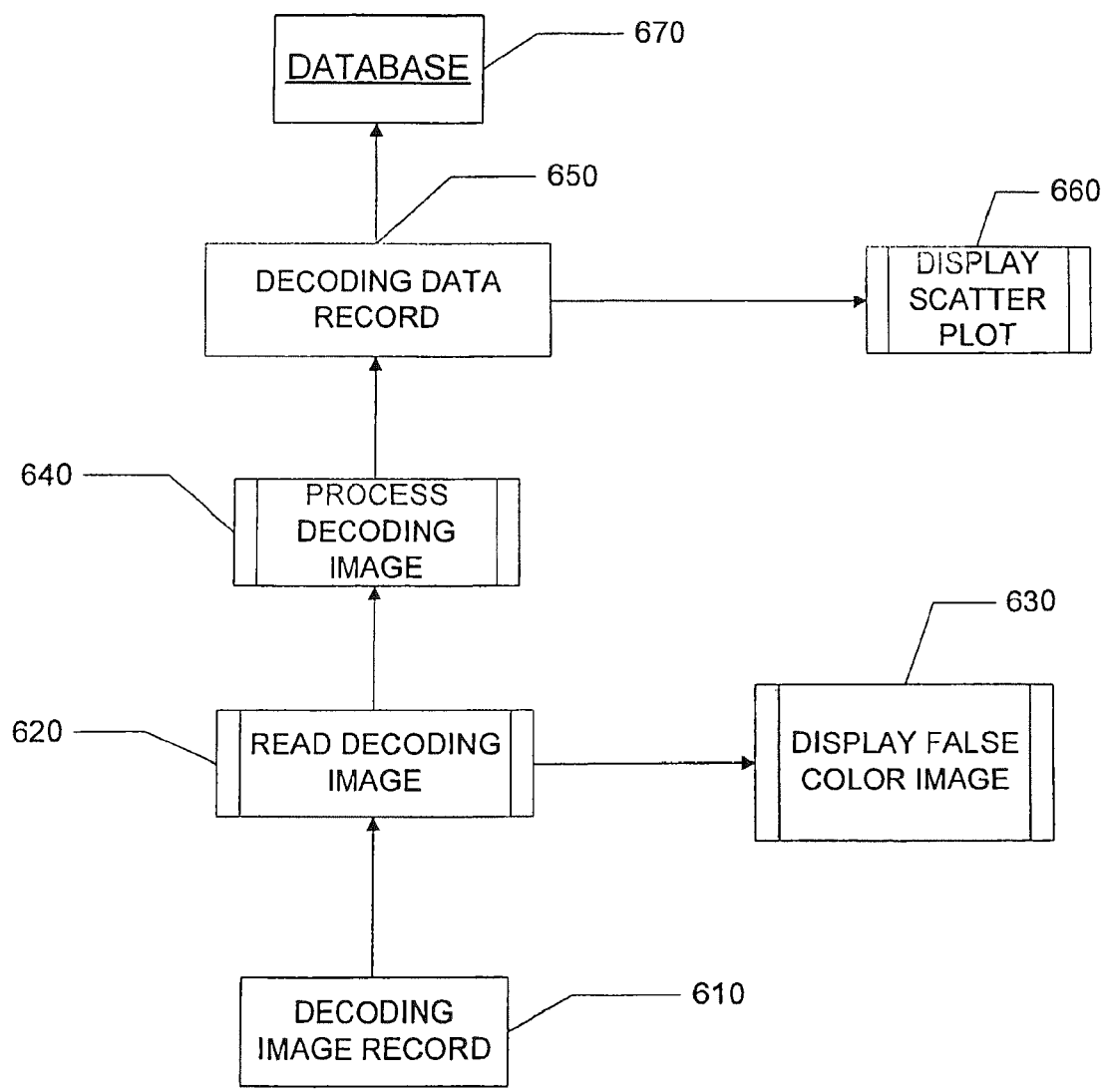
FIG. 6 is a flowchart of the formation of a decoding image and decoding data records where the resulting information can be stored in a database.

An image processing program (designated "DECODER"), which can be run, for example, on the Microsoft Operating system, e.g., Windows 98 or 2000, and which contains functions to display, process, save and print "multicolor" sets of multiple microarray images in an integrated graphical user interface (GUI) and to generate a decoding data record which may be submitted for further analysis to the ANALYZER, residing either on the same computer or on a separate computer. This program can be readily implemented by those skilled in the art, using the outlines herein. As illustrated in FIG. 6, the operation of the DECODER comprises reading the Decoding Image Record (610, 620), rendering and displaying decoding image(s) (630), and processing decoding image(s) (640) to create a Decoding Data Record (650), display scatter plots (660) and update databases (670).

Figure 7:
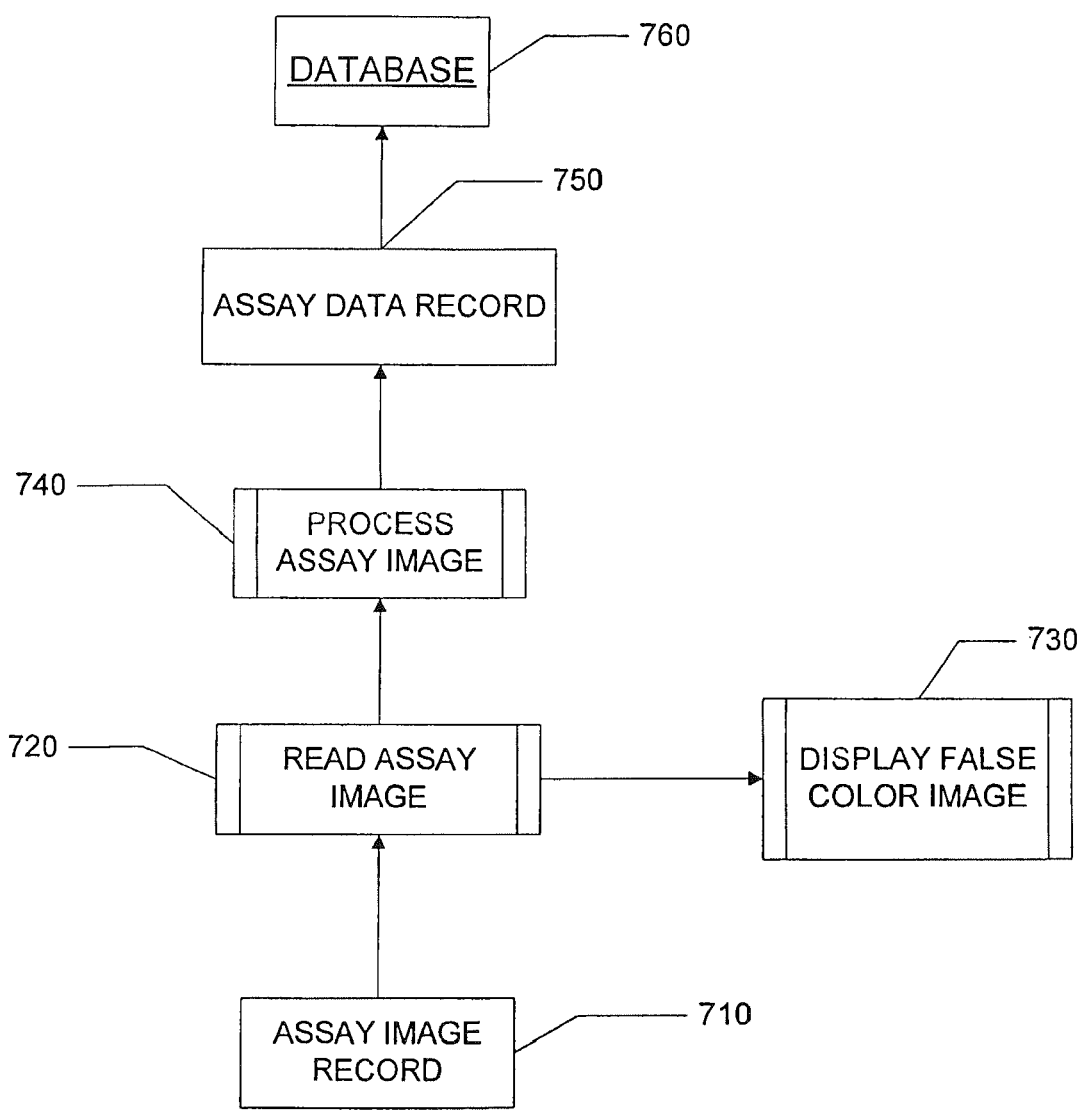
FIG. 7 is a diagram illustrating the, reading and processing of an assay image and recording of an assay data record, where the resulting information can be stored in a database.

Another image processing program (designated READER), which can be run, for example, on the Microsoft Operating system, e.g., Windows 98 or 2000, and functions to display and to process pairs of assay images acquired so as to generate an assay data record which may be submitted for further analysis to the ANALYZER, residing either on the same computer on a separate computer. As illustrated in FIG. 7, the operation of the READER comprises reading the Assay Image Record (710, 720), rendering and displaying assay image(s) (730), and processing assay image(s) (740) to create an Assay Data Record (750) and update databases (760).

Figure 8:
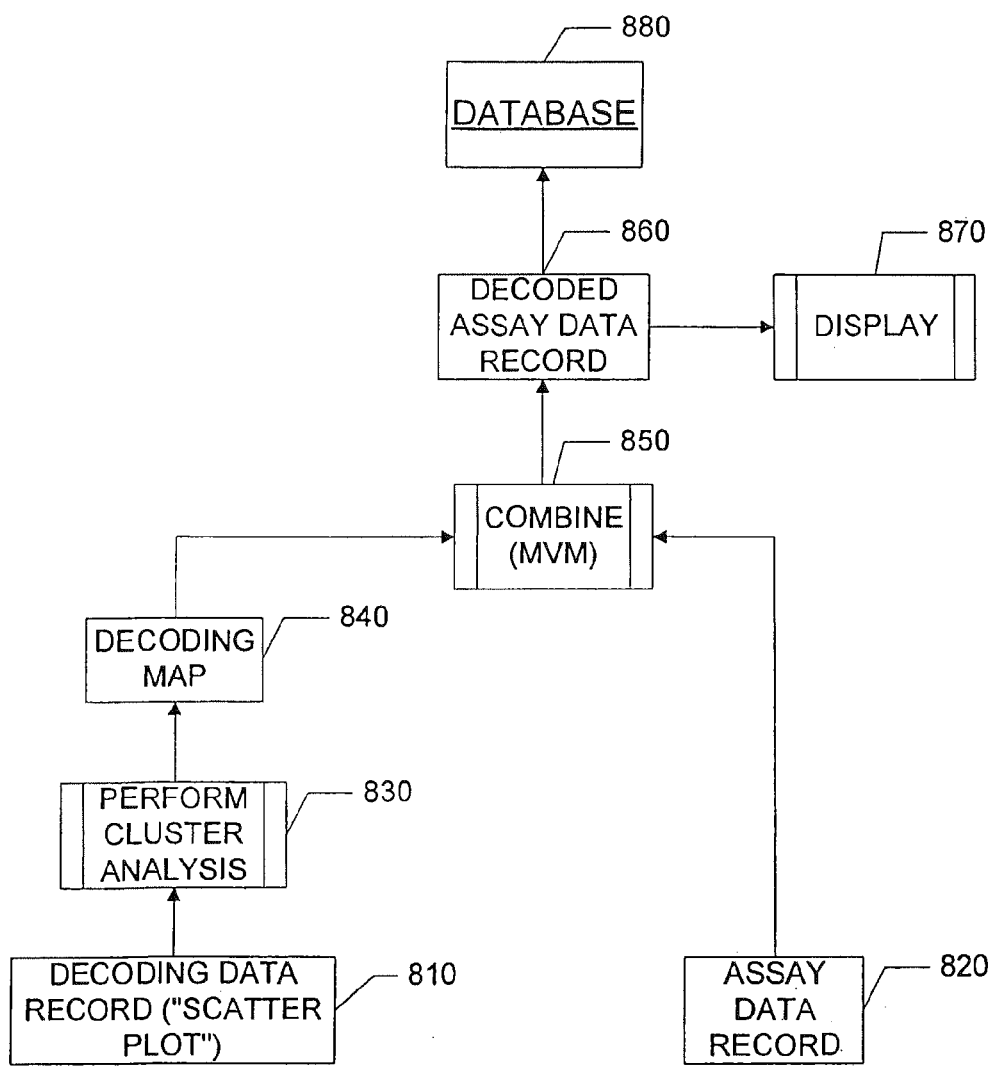
FIG. 8 is a flowchart illustrating the recording, analysis and decoding of assay data, and combining with an assay data record to generate a decoded assay data record, where the resulting information can be stored in a database.

ANALYZER is an analysis program. As illustrated in FIG. 8, ANALYZER receives input from DECODER, in the form of a Decoding Data Record (810), and READER, in the form of an Assay Data Record (820), and comprises functions to perform further analysis including: cluster analysis (830) to create a decoding map (840). The decoding map is combined (850) with an assay data record so as to produce a Decoded Assay Data Record (860) which is displayed (870) in a variety of formats and stored in a database (880).

ANALYZER, DECODER and READER may reside on separate computers which may communicate by way of a data network. In this manner, data from assays can be received from a remote site but can be decoded and analyzed at another site. In such embodiment, DECODER and ANALYZER may be integrated into a single program or loaded onto the same computer.

IChipReader provides a COM interface in the form of a dynamically linked library linking the functions of DECODER and READER.

This image analysis system has the following advantages.

Reliability: Robust algorithms have been designed in order to handle images of widely varying quality encountered in practice, including images exhibiting very low contrast or variations in contrast across the image, significant noise and corruption of edges or features, or displacement and misalignments between multiple images of a given array. These robust algorithms ensure the reliability of the results produced by the analysis.

Accuracy: The entire sequence of processing steps is performed without human intervention, thereby avoiding error and enhancing ease-of-use.

Speed: Algorithms have been designed for efficiency, and functions have been integrated so as to minimize processing time. A chip displaying a single array can be processed in as little as 4 seconds.

Productivity and throughput: Sets of images may be analyzed in batch mode.

Ease-of-use and convenience: The GUI package provides convenience and flexibility in controlling all system functions.

Functions and capabilities provided by these systems including processing, analyzing, transmitting and storing images are elaborated below.

II.1 Array Segmentation and Extraction of Signal Intensities

Image processing may be applied to each of the one or more constituent images of a composite image in the decoding data record or assay data record to segment the image and extract a textual representation of the signal intensity distribution within the array. This representation would serve as input for further analysis.

In certain embodiments, decoding and assay images or the corresponding data records are analyzed to obtain quantitative data for each bead within an array. The analysis invokes methods and software implementing such methods to: automatically locate bead arrays, and beads within arrays, using a bright-field image of the array as a template; group beads according to type; assign quantitative intensities to individual beads; reject processing "blemishes" such as those produced by "matrix" materials of irregular shape in serum samples; analyze background intensity statistics; and evaluate the background-corrected mean intensities for all bead types along with the corresponding variances.

II.1.1 Referenced Arrays

Referenced arrays are located in designated positions, and in designated orientations, with respect to features designed into patterned substrates in accordance with methods previously disclosed in PCT/US01/20179, U.S. Pat. No. 6,251,691 and U.S. patent Ser. No. 10/192,352. For example, a locus of low impedance on a substrate may be designed to collect particles using the LEAPS™ method and may further contain a central recess grid to mechanically immobilize microparticles. See U.S. Pat. No. 6,251,691.

Specifically, in one embodiment, following completion of AutoCentering and AutoFocusing as described above, the system makes a record, in both the "record Decoding Image" and the "record Assay Image" modes, of both the brightfield image and one or more color images of the array, the color images being recorded following selection of the desired filter settings as described above. In one embodiment, color images in the "record Decoding Image" mode are recorded in a "BLUE" and in a "GREEN" channel selected by respective filter combinations (Blue Channel: excitation filter: 405 nm (20 nm); emission filter: 460 nm (50 nm) and beam splitter: 425 nm (long pass), Green Channel: excitation filter: 480 nm (20 nm); emission filter: 510 nm (20 nm) and beam splitter: 495 nm (long pass)) and one color image in the "record Assay Image" mode is recorded in a "RED" channel selected by a filter combination Red Channel (excitation filter: 640 nm (30 nm); emission filter: 700 nm (75 nm) and beam splitter: 660 nm (long pass)). The excitation filters transmit only those wavelengths of the illumination light that efficiently excite a specific dye, and an emission filter attenuates all the light transmitted by the excitation filter and transmits any fluorescence emitted by the specimen, and a beam splitter reflects the excitation light but transmits the emitted fluorescence (the figures in parenthesis indicate the width of the band for each filter). Therefore, the AIS system, in either "record Decoding Image" mode or "record Assay Image" mode, permits recording of images in two or more color channels.

Processing of images recorded from referenced arrays may be performed by extracting a reference "mesh" or "grid" structure, where individual fields in the grid include beads and the outer dimensions of the grid correspond with the dimensions of the referenced array. The principal operations common to the processing of Decoding Images and Assay Images include segmentation to locate array boundaries, mesh/grid delineation, image registration (or alignment) and extraction of intensities, as elaborated below. Following completion of processing steps, further analysis is performed by constructing a decoding map from two or more decoding images using a cluster algorithm and by merging decoding and assay data record to produce decoded assay data record. Partial or complete results and related information may be exchanged between two or more parties, as further elaborated herein.

In the "process Decoding Image" mode, the following operations, as shown in Table III, are utilized. Table III shows the pseudocode for an exemplary processing of a decoding image.

TABLE III

LoadImage (BrightField Image);
FindBoundary (BrightFieldImage, RotAngle );   / using brightfield image, find array boundary and angle of misorientation with respect to display edges /
RotateImage(BrightFieldImage, RotAngle);
FindGrid (BrightFieldImage, Grid)    / locus of local intensity minima /
FOR (each decoding image be processed) {
   LoadImage (Fluorescence Image);
   RotateImage (Fluorescence Image, RotAngle);
   AlignImage(FluorescenceImage);    / align fluorescence image with bright field image /
   OverlayGrid ( );
   ReadIntensityDistrib(DecodingDataRecord, SampleMesh, Grid, FluorescenceImage);
}

These steps are followed by the step of creating a scatter plot from two or more decoding images and performing a cluster analysis to establish a decoding map.

These steps are elaborated below.

In the "process Assay Image" mode, the pseudocode for the processing of an assay image, as illustrated in Table IV, are used.

TABLE IV

LoadImage (BrightField Image);
FindBoundary (BrightFieldImage, RotAngle );    / using brightfield image, find array boundary and angle of misorientation with respect to display edges /
RotateImage(BrightFieldImage, RotAngle);
FindGrid (BrightFieldImage, Grid)           / locus of local intensity minima /
FOR (each assay image to be processed) {
   LoadImage (AssayImage);
   RotateImage (Assay Image, RotAngle);
   AlignImage(AssayImage);     / align assay image with bright field image /
   OverlayGrid ( );
   ReadIntensityDistrib (AssayDataRecord, SampleMesh, Grid, AssayImage);
}

Histogram expansion is applied to brightfield and color images prior to finding boundaries, locating grids and aligning images; only the intensity extraction is performed on the 16-bit image as originally recorded. The principal operations are implemented using standard methods (Seul, O'Gorman & Sammon, "Practical Algorithms for Image Analysis", Cambridge University Press) as follows.

FindBoundary—Array edges in the brightfield image (and optionally any of the color images) are located using a standard Sobel y-gradient operator image for left and right edges and a standard Sobel x-gradient operator for top and bottom edges. Using these edges, the location of the array and its misorientation with respect to the image display boundaries are computed. For future use, the array is rotated to bring it into alignment by with the image display. Prior to edge detection, noise is filtered by applying six iterations of a morphological "Open" operation, which is an image processing technique. See Seul, O'Gorman & Sammon, supra.

Mesh/Grid Construction—A grid or mesh delineating intensity maxima ("peak") is extracted by tracing the locus of local intensity minima ("valley") within the brightfield image. This locus defines a mesh or grid such that each field in the mesh delineates a local intensity maximum associated with a bead or with a recess provided in patterned substrates. In this manner, the grid traces around each of the beads, and includes one bead in each segment of the grid.

Figure 15:
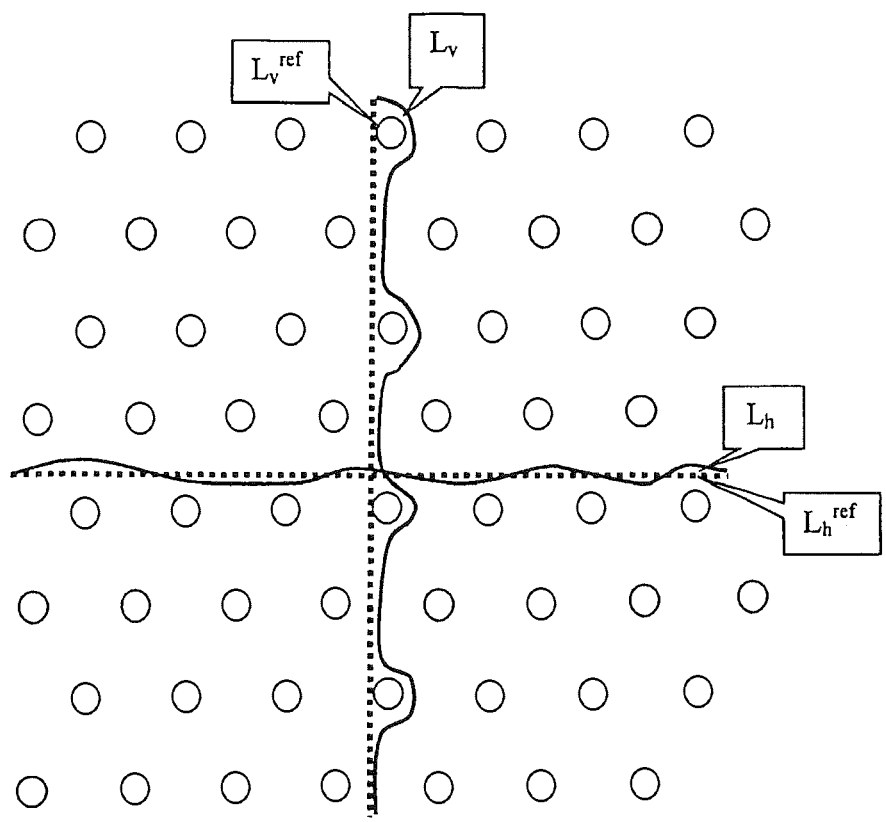
FIG. 15A illustrates mesh overall orientation with the shortest path algorithm, wherein $L_h^{ref}$ and $L_v^{ref}$ are the reference lines. By applying shortest path, $L_h$ and $L_v$ are found. It can be seen that when $L_h$ is shorter than $L_v$, then the overall orientation of the mesh is 0 degrees.
FIG. 15B illustrates vertical line grid partition by the shortest path algorithm.
Figure 15:
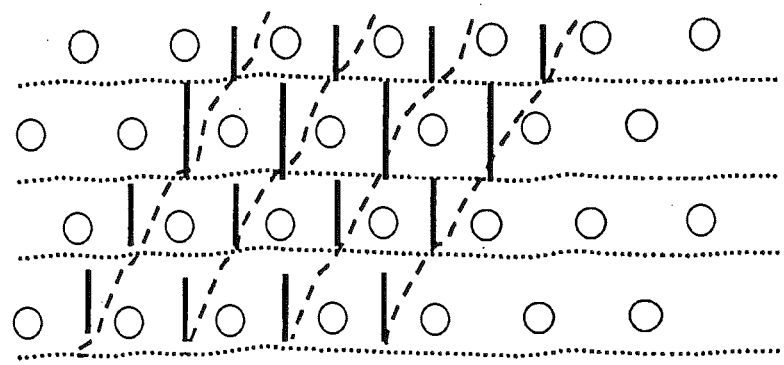

To implement the mesh construction, the problem is mapped to Dijkstra's "shortest path" algorithm (see Introduction to Algorithms, T. Cormen, C. Leiserson et al., The MIT Press) well known in the fields of computational geometry and combinatorial optimization, by ascertaining the intensities of image pixels with values of vertices in a graph. The algorithm finds the mesh, also referred to as a grid, as an optimal path as follows:

Pre-Process Image:
  Compute the external gradient image by subtracting a dilated image from the original image.
Determine Overall Orientation, Either Horizontal or Vertical
  As illustrated in FIG. 15A, provide horizontal and vertical reference lines of known length to determine the orientation of the underlying hexagonal grid, compute shortest paths for the two reference lines and compare to corresponding reference line lengths by forming. The ratio closes to unity indicates either horizontal or vertical orientation.
Find Horizontal Grid Partition:
  Replicate reference lines by shifting by unit mesh size, then compute shortest path to determine actual grid line. Continue until replicated line falls outside array boundary.
Find Vertical Grid Partition:
  As illustrated in FIG. 15b, find the shortest path of a diagonal line—depending on overall orientation—oriented at either 30 degrees or 60 degrees with respect to the horizontal lines in the case of an anticipated underlying hexagonal lattice of average intensity maxima. Compute intersections of the diagonal lines and every horizontal line given the intersections of the diagonal lines and two consecutive horizontal lines, vertical lines will be located at the midpoint of these intersections.
Post-Process Grid:
  Grow or shrink grid defined by the totality of the horizontal and vertical lines to the expected array boundary; correct grid stagger.
Store Grid:
  Store grid coordinates in a file.
Image Registration—Given a grid, a registry of the brightfield image with one or more color images ensures proper alignment by eliminating possible misorientation and translation ("shifts") between the multiple images recorded from a given array. One source of such shifts is the wavelength-dependent refraction introduced by standard fluorescence filter combinations. Registration aligns the assay and decoding images.

Misorientation is eliminated by rotation to bring a given image into alignment with a reference such as the brightfield image grid. An alternative for aligning images without reference to a brightfield image is described below.

Assuming only translational displacement, the system can invoke the following fast algorithm. To determine horizontal displacement ("X-shift"), construct intensity profiles along vertical scan lines within the array boundary; similarly, to determine vertical displacement ("Y-shift"), construct intensity profiles along horizontal scan lines within the array boundary. Next, construct horizontal and vertical profiles along lines displaced from the first set by one respectively one horizontal or one vertical mesh unit. The peak in the profile determines the image shift.

The methods herein are limited to shifts between images of less than half of the mesh size, by the optical subsystems of the system including the CCD camera used herein. If larger shifts are encountered, image registration may be off by one mesh unit in row and/or column dimensions. A Minimal Variance Matching algorithm described below is utilized to correct larger misalignments.

Intensity Extraction. Following completion of image registration, in one embodiment, intensities are extracted from each color image by sampling the interior, and not the exterior, of each field of the mesh/grid with an averaging filter mask of suitably chosen size to fit into the interior of each mesh field. Each intensity value is optionally corrected by subtracting a supplied background value. One method of supplying the background values is to record it as an average of pixels values from an area of the image outside the mesh/grid boundary.

In contrast to widely used conventional methods that invoke peak finding and peak fitting algorithms to locate object positions, the present method offers substantial advantages of processing speed.

Extracted intensities are stored—optionally in binary form—in a one-dimensional array of length L, L denoting the number of units of the grid/mesh constructed in the course of segmentation. This one-dimensional array can be mapped onto the grid or mesh to associate each intensity value with a unique coordinate within the bead array. For example, the following structures may be used:

```
float intensity[4012];      /** array holding 4012 intensity values **/
Struct Grid{
    int leftUpX,
    int leftUpY,
    int rightDownX,
    int rightDownY};        /** structure representing one grid field **/
Grid grid[4012];            /** array holding 4012 grid fields **/
```

Eliminating Reference to Brightfield Image. In certain embodiments, one may eliminate reference to the brightfield image in the course of image processing, notably during the step of eliminating image misalignment, and indeed to eliminate the step of recording the brightfield image altogether. In that case, the step of aligning color images with the display boundaries invokes information extracted directly from the color images.

The approach is conceptually as follows. Given a color image, construct horizontal and vertical intensity profiles by respectively projecting image intensities to the top-most and left-most scan line in the display, then evaluate the intensity variation in each profile. Next, rotate the color image by a pre-defined angle and repeat the previous construction. Continue to rotate until the profiles exhibit maximal variations, then reduce the step size in rotation angle and reverse the direction of rotation until the optimal rotation angle is found.

This procedure is significantly improved when information about the array geometry is available a priori. For example, in one embodiment of referenced arrays, a hexagonal geometry with specific choice of nearest neighbor separation, a, and alignment of principal axes with the chip edge is chosen. Then, the desired alignment is characterized by one of the profiles assuming the form of a periodic variation with a single periodicity, a, and the other profile assuming the form of a superposition of two phase-shifted periodic functions, both with periodicity, a*cos 30°. Horizontal and vertical profiles produced by such an array at a given misalignment angle thus may be analyzed by fitting each to a superposition of two trial functions and obtaining the angle of misalignment from the fit.

II.1.2 "Non-Referenced" Arrays

Decoding and Assay Images. To perform a multiplexed binding assay in accordance with the READ™ process, the array is first imaged by multicolor fluorescence, to determine the color code of constituent beads which uniquely correspond to the chemical identity of the probe displayed on the bead surface; second, to record the fluorescence intensity which indicates the amount of probe-target complex formed on each bead surface in the course of the binding or hybridization assay. The process of image detection and bead decoding is described in PCT/US01/20179 (WO 01/98765), incorporated herein by reference in its entirety.

Quantitative Analysis. Image analysis algorithms that are useful in analyzing the data obtained with the READ process disclosed herein may be used to obtain quantitative data for each bead within an array, as set forth in PCT/US01/20179, incorporated herein by reference. In preferred embodiments, data are obtained from the decoding and the assay images, or preferably from the corresponding decoding image record and assay data record by application of certain algorithms. These algorithm may be used to obtain quantitative data for each bead within an array. The analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances. Using calibration beads that are included in the assay, intensities are converted to an equivalent number of bead-bound fluorophores.

II.2 Representation and Encryption of Array Configurations—ChipID

II.2.1 Covering. Given a set of probe molecules of types $P=\{p(1), \ldots, p(k), \ldots, p(n)\}$ and a set of tags, $T=\{t(1), \ldots, t(k), \ldots, t(n)\}$, the former, for example in the form of oligonucleotides of defined length and sequence, the latter for example in the form of color codes associated with a set of beads, one defines a one-to-one mapping of T onto P whose image represents a covering, C:=C (P) of the set P. The covering is obtained by attaching probes in set P to color-encoded beads in set T.

In certain embodiments, encrypted coverings serve to conceal the identity of probe molecules associated with tags by revealing, for each probe molecule, only a label or pointer that is logically linked to that probe molecule, but not the probe identity itself. This is disclosed only by a "de-covering" process.

II.2.2 Encoding Random Array Configurations

The random assembly of pooled beads of different types into a planar array creates a specific configuration, thereby defining a "random encoding", E, as follows. Given a set of tags, $T=\{t(1), \ldots, t(k), \ldots, t(n)\}$, for example in the form of color codes associated with a set of pooled particles, define E as the mapping of T onto a set of positions, $V=\{v(1), \ldots, v(l), \ldots, v(L)\}$, constructed as follows: from each of n reservoirs of particles, each reservoir containing particles that are uniquely associated with one tag in accordance with $T=\{t(1), \ldots, t(k), \ldots, t(n)\}$, draw r(k) (indistinguishable) particles and place them into r(k) positions randomly selected from a set $V=\{v(1), \ldots, v(l), \ldots, v(L)\}$. In a preferred embodiment, V corresponds to the vertices of a rectangular array, $\{(i,j); i=1, \ldots, I, j=1, \ldots, J\}$ or, equivalently, $\{1; l=1, \ldots, L:=I*J\}$, of designated positions ("traps") in a silicon substrate.

In certain embodiments, encoding serves as a further level of encryption to conceal the identity of tags which is revealed only by the decoding process. In addition, standard encryption techniques may be applied to further conceal encoding and covering information. Decoding of the array configuration identifies the tag assigned to each of the positions within V. For example, each such color code, identified by a unique tag index, may be obtained by combining fluorescent dyes of fundamental colors, R, G and B, for example, in specified ratios to produce beads producing fluorescence signals of intensities $(I_R, I_G, I_B)$, for example, in the respective color channels, R, G and B. The system described herein can maintain this information in a separate configuration file, which is generated in conjunction with the production of bead libraries.

Representations. In one embodiment, encoding is achieved by creating spectrally distinguishable particles by way of staining them with two or more dyes in accordance with one of several possible possibilities. For example, several fluorophore tags in the form of dyes, Red (R), Green (G) and Blue (B), for example, may be combined in a variety of fixed R-G-B molar ratios or may be combined in binary (or other) fashion, each dye being either present or not present in any given particle type. Decoding of an array of color-encoded particles is performed as described herein by recording a set of images showing fluorescence intensities in separate color channels for each of the fundamental dyes and determining molar ratios by analyzing intensities in the various color channels.

The information from multiple decoding channels may be represented in a merged decoding intensity array which forms part of the Decoding Data Record described herein, by listing, for each position v(l), 1 . . . l . . . L, a set of intensities $(I_R, I_G, I_B)_l$, for example, or listing relative abundances that are obtained by normalizing intensities by suitable internal standards. Optionally, to obtain a compact integer representation, intensities may be represented in binary form, $I=2^p$, $0 \leq p \leq 16$ so that a set of exponents $(p_R, p_G, p_B)_I$ may be stored for each position.

Further analysis, performed as described herein in subsequent sections, serves to construct a decoding map. This map is composed of clusters, each cluster representing one spectrally distinguishable particle type which in turn is defined by a triplet of fundamental tags, such as $(I_R, I_G, I_B)$. Once the decoding is in hand, clusters may be given a simple index which now serves as a tag index. That is, the triplet is replaced by a simple tag index. Accordingly, the random encoded configuration generated by E may be represented in the form of the random sequence of L=3r(k) tag indices assigned by the encoding E to positions $(v(1), \ldots, v(l), \ldots, v(L))$. In certain embodiments, it will be convenient and useful to sort this sequential representation by tag index so as to obtain a one dimensional array of n lists, the k-th such list containing the sequence of r(k) array positions occupied by tag k. If the positions are identified by the corresponding vertex array index, this provides a particularly compact representation.

Alternatively, a representation in the form of a 1-d array of length L of tag indices also may be convenient. For example, the configuration of an array composed of 4,096 or 212 beads of 128=27 types, could be stored in 4k*2 Bytes=8 kB of non-volatile memory which could be packaged with the carrier.

Individual Array Configurations: IntrinsicChipID. In a preferred embodiment of a random encoded array assembled on a silicon chip substrate, the array configuration, in any of the aforementioned representations, provides an identifying tag for the substrate. See U.S. patent application Ser. No. 10/365,993 "Encoded Random Arrays and Matrices." filed Feb. 13, 2003, incorporated by reference. Each such InstrinsicChipID is drawn from the number, S, of distinguishable configurations of a random encoded array of I*J=L vertices, given by the number of ways in which n (unordered) samples of r(k) (indistinguishable) particles of type t(k), 1≤k≤n, may be distributed among L positions:

$$S(L; n; r(k), 1 \leq k \leq n) := L!/r(1)!r(2)! \ldots r(k)! \ldots r(n)!$$

Illustrating the large number of possible combinations is the fact that an array of L=16 positions, composed of n=4 bead types, where each type is represented four times (r(1)= ... r(4)=4), can display S(16; 4; r(k)=4; 1≤k≤4)=16!/(4!)^4, or approximately 63 million configurations. The InstrinsicChipID may be cast in any of the representations discussed above.

Degree of Randomness: Autocorrelation Function of Tag Sequence. Indeed, the degree of randomness of a given bead array is readily ascertained by constructing the autocorrelation of the tag sequence corresponding to the random configuration of encoded beads within the array as elaborated above. For example, a random sequence of length 22 and composed of three tags, R, G, B with relative abundance $7/22=1/3$, will produce an autocorrelation function, g, of this type with the following behavior near the origin:

| | | |
|---|---|---|
| Shift: −1 | RGGBRGRRBRGRBRGBBRGGBG<br>RGGBRGRRBRGRBRGBBRGGBG | g = 3 |
| Shift: 0 | RGGBRGRRBRGRBRGBBRGGBG<br>RGGBRGRRBRGRBRGBBRGGBG | g = 22 |
| Shift: +1 | RGGBRGRRBRGRBRGBBRGGBG<br>RGGBRGRRBRGRBRGBBRGGBG | g = 3 |

Scoring each tag match in the autocorrelation as 1, each tag mismatch as 0, it is readily seen that the (normalized) autocorrelation function of the random tag sequence will exhibit a sharp peak and will drop—within a single unit shift—to the average value of $\sim(1/r)^2$, r denoting the average redundancy of each tag. This property of random encoded arrays will serve to construct a robust "matching by variance minimization" algorithm to combine decoding and assay data records, as described herein.

II.3 Image Analysis

Completion of the aforementioned image processing steps yields a compact representation of the intensity distributions in decoding and assay images which facilitates further analysis. This analysis includes the steps of generating a decoding map from the set of decoding images and combining ("merging") decoding and assay images to generate final assay results using a matching algorithm further elaborated below.

II.3.1 Construction of Decoding Map by Cluster Analysis

A decoding map assigns each bead located in the processing of a decoding image to a unique group in accordance with its unique tag. For example, color-encoded beads will be grouped by color and/or by intensity of each of two or more encoding colors, as assumed here for clarity in the exposition of the clustering algorithm. It will be apparent that other codes are possible here and will be used in analogous fashion. The system herein may include two or more clustering algorithms.

II.3.1.1 Matching to Map Template

This algorithm anticipates a decoding map template, constructed manually or otherwise provided, which provides seed locations, each anticipated group or cluster in the decoding map corresponding to one such seed. This is particularly advantageous in the situations commonly encountered in practice involving analysis of a decoding image recorded from bead arrays of the same batch or lot. That is, the number of anticipated clusters, and their respective approximate central locations, are known a priori. Assuming, for purposes of illustration, ratio encoding by two encoding colors, the algorithm produces a partition of a given scatter plot of decoding intensities which is first converted into a two-dimensional histogram.

The map template matching algorithm first generates a two-dimensional histogram image of the input data, optionally providing smoothing to the histogram image to eliminate noise. Given the two-dimensional histogram, the decoding group is generated using a "watershed" algorithm, well known in the art in connection with image segmentation, which treats the intensity histogram as a topographical map showing local elevation as function of position. Starting at the lowest point, the "water level" is now gradually increased until "water" starts to spread over two previously separate compartments. A "dam" is constructed at the "overflow" position. The set of dams so constructed represents the set of segment boundaries.

To implement these steps of generating the decoding map, the map template matching algorithm uses three auxiliary objects: a priority queue, a stage (of processing) image and a label image. The priority queue maintains individual pixels in accordance with their intensity values as obtained from the two-dimensional histogram of the input scatter plot, keeping the pixel with the maximal value at the top. The stage image serves to track the stage of pixel assignment: any given pixel either is or is not assigned to a group or cluster. The label image serves to track the group identity of each assigned pixel.

The algorithm proceeds as follows. For each given seed, initialize the corresponding pixel in the label image by assigning it the seed label, add its eight nearest neighbors to the priority queue and mark each of these pixels "assigned" in the stage image. Next, pop the top pixel from the queue and inspect its eight nearest neighbors, ignoring unassigned pixels and checking whether all "assigned" neighbors have the same label. If so, mark the pixel with that label, otherwise, leave the pixel unmarked. Finally, add to the queue all non-zero neighbors not currently in the queue and pop a new element. Continue until queue is empty—at which point the label image shows the group assignment for each pixel.

The resulting partition assigns each data point in the scatter plot to one and only one of the groups ("clusters") identified by the set of given seed locations. Two or more of such scatter plots are processed if three (or more) colors are used for encoding. The algorithm performs the operations as illustrated in Table V. Table V shows the pseudocode for the operation of constructing a Decoding Map by way of template matching.

TABLE V

```
CreateScatterPlot(Image, IntensityArray(FirstColor),
IntensityArray(SecondColor));
        /** 2d Plot of Intensities extracted from Decoding Images in
            different Selected color channels **/
ConvertScatterPlotToTwoDimHistogram(Image);
SmoothImage(Image, Kernel);    /** apply 5*5 Smoothing Filter **/
SetMapTemplate(MapTemplate); /** provide map template **/
GetSeedLocations(MapTemplate, ClusterSeeds);
GenerateDecodingMap(ClusterSeeds);
```

II.3.1.2 Fast Clustering Algorithm

The system described herein also includes a fast algorithm that invokes graph theory to construct a two-dimensional decoding map without the aid of a template. The algorithm converts the input scatter plot of intensities into a "distance graph," each data point in the scatter plot representing one node in the graph, and each such node being connected by one edge to its K nearest neighbors (by Euclidean distance). Each edge is assigned a weight that is proportional to its length, and each node is given a value computed from the weight of the largest edge connected to that node.

The algorithm comprises the following steps. First, load scatter plot and convert it to a distance graph image. Process the graph image by applying a morphological Open operation to each connected graph—the steps of erosion and dilation constituting the open operation will alter node values. Next, for each node in turn, eliminate all edges whose weight exceeds the node's new value. Then, partition the graph into connected components, a connected component or cluster being defined as a sub-graph of connected nodes—each node within a connected subgraph can be visited by traversing edges. Finally, filter out small groups and split large groups into two groups if necessary. The algorithm thus performs the following steps, as illustrated in Table VI. Table VI shows the pseudocode for the operation of constructing a Decoding Map by fast cluster analysis.

TABLE VI

```
CreateScatterPlot(Image, IntensityArray(FirstColor),
IntensityArray(SecondColor)) ;
ConstructDistanceGraph(GraphImage, Image);  /** assign value to each
                                                node **/
Open(GraphImage);
For each(Node in the GraphImage){    /** process all nodes in the
                                         graph **/
    For each(Edge of the Node){      /** process all edges of a node **/
        If( Edge > Node){
            DeleteEdge( );
        }
    }
}
PartitionGraph(GraghImage);          /** partition graph into
                                         connected subgraphs
                                         ("clusters") **/
PostProcess(GraphImage);
```

Three-Color Encoded Objects: "Stacked" Decoding Maps. The clustering algorithm is applied to handle multi-dimensional cluster analysis for populations constructed as stacked two-dimensional clusters by preceding the clustering operation with a sorting step. In stacked two-dimensional clusters the third decoding image acquired in a case of encoding by three-color combinations will have one or more discrete intensity levels. Considering first the case of just a single intensity level, particles are readily sorted into two groups, namely those containing the third dye (labeled ON) and those not containing the third dye (labeled OFF) to obtain a stack of two-dimensional scatter plots which are individually analyzed to generate two corresponding decoding maps. In practice, this operation is performed using the DECODER as follows. First, generate a two-dimensional scatter plot for the original two dyes, encoding colors, designated G and B. This "G-B" plot represents an intermediate result that corresponds to the projection of the three-dimensional "R-G-B"space onto the "G-B" plane. To split this projected scatter plot into its constituent components, generate a two-dimensional scatter plot just for third color, designated R, in the "R-R" plane by providing two copies of the decoding image recorded in the R-channel. The "R-R" plot will have the same size (and number of eventual clusters) as the "G-B" plot (containing, after all, images of the very same objects). The "G-B" plot is now split into two plots, one containing only points corresponding to "R-OFF", the other containing only points corresponding to "R-ON". A (two-dimensional) decoding map is now constructed for each plot using one of the algorithms described above. This strategy is readily generalized to populations encoded using multiple levels of a third color.

II.3.2 Combining Assay and Decoding Images

The identity of the binding agent of the binding agent-analyte complex is determined by decoding. This step entails comparison of decoding image(s) and assay image(s). That is, the assay image is sampled in accordance with the cluster information in the decoding map to group assay signals by bead type and hence by encoding tag as described above. A robust matching algorithm ensuring alignment of decoding images and assay images is described below.

Decoding may be carried out at the user site or at a central location. For example, decoding images—in a suitable representation such as merged decoding intensity arrays—are made available to the user, either in the form of text files on a recording medium that is distributed along with bead arrays or in the form of a downloadable file available by way of authenticated access to a central database. Alternatively, decoding may be carried out on a central server after uploading of the assay image from the user site. Transaction protocols for this and related mode of data communication are disclosed below.

Matching by Variance Minimization (MVM). By construction, constituent beads of a randomly encoded bead array are randomly dispersed over the array. Assay signals recorded from a set of beads randomly drawn from all subpopulations or types of beads, these beads displaying different types of probes, will exhibit an inter-population variance, V, that reflects the differences in the corresponding probe-target molecular interactions. Assuming equal abundance of all bead types, this inter-population variance may be approximated by the variance associated with the distribution of the mean assay signals evaluated over each subpopulation, namely:

$$V = \sum_j (<<I>> \cdot <I>_j)^2,$$

$<I>_j$ denoting the mean assay signal of the j-th subpopulation and $<<I>>$ denoting the mean of the $<I>_j$. In contrast, assay signals recorded from a set of beads drawn from the same subpopulation, these beads displaying the same type of probe, will exhibit an intra-subpopulation variance, v, that reflects aspects of characteristic remaining chemical heterogeneities such as bead size, density of probes displayed on beads, assay binding efficiency, etc, given that all probe-target interactions within the subpopulation are nominally identical for each subpopulation; the intra-population variance has the form:

$$v = \sum_k (<I> - I_k)^2,$$

$I_k$ denoting the assay signal recorded from the k-th bead within the subpopulation. Except in special circumstances, assay signals recorded from different subpopulations will be uncorrelated, and the variance, V, will exceed v:

$$V \gg v$$

It is this insight which forms the basis for a robust "matching by variance minimization" algorithm by which to perform the cross correlation of decoding and assay images recorded from a random array and to resolve the task of perfectly aligning the two (or more) images of interest in the absence of fixed alignment aides and in the presence of edge-corrupting noise. That is, only in the correct alignment of decoding image and assay image are assay signals within the assay image sampled over members of the same subpopulation. In one embodiment, the alignment is performed by monitoring the variance, computed for one or more specific subpopulations of beads that may be included in the array for this purpose, as the assay image is shifted with respect to the decoding image.

As discussed herein in previous section II.2.2, even a single step displacement will completely scramble the sampling and mix assay signals from multiple subpopulations. Accordingly, the correct alignment, even in the presence of considerable edge corruption, is robustly indicated by minimizing the variance of assay signals over a subpopulation as a function of relative displacement. In practice, "dark" particles or objects are filtered out during this matching step to eliminate erroneous contributions to the variance. The FilterDarkBeads function is required to eliminate from the assay image objects or microparticles which do not contribute a measurable signal because—while the center of bright objects coincides with the maximum in the intensity profile it coincides with the minimum in the intensity profile for dark objects. This can lead to errors in aligning assays and decoding images. In practice, each array is designed to include one or more reference subpopulations displaying positive or negative control probes which are designed to generate a signal of known magnitude so as to ensure that indeed v≪V. These one or more reference subpopulations are sampled to minimize the corresponding subpopulation variances, v, as a function of displacement from perfect alignment. That is, v is evaluated as the assay image grid is shifted relative to the decoding image grid. If the condition v≪V is not satisfied, the algorithm produces a warning to indicate a possible problem with image quality and provides a choice to abandon further analysis.

As illustrated in FIGS. 9A and 9B, there are seven possible misaligned positions if the search is confined to single row and single column misalignments, namely: (−1, −1), (−1, 1), (−1, 0), (0, 0), (1, 0), (−1, 1), (1, 1); that is, to account for the stagger introduced in the image grid derived from a hexagonal lattice (910, 920), seven distinct positions are checked, as illustrated in FIG. 9C.

The Minimal Variance Matching algorithm operates on Decoding and Assay Data Records and evaluates the desired variance as a function of unit shifts applied to the two images represented in the respective data records. Table VII shows the pseudocode for the operation of combining decoding and assay images by way of Matching by Variance Minimization.

TABLE VII

```
LoadDecodingData(DecodingDataRecord, DecodingMap);
LoadAssayData(AssayDataRecord, IntensityArray);
MinVariance = −1000;
MinVarianceLocation = 0;
/** Check Variance Produced by 7 Possible Unit Displacements - see
Text **/
For (i=0; i< 7; i++){
    ShiftGridPosition(i);
    FilterDarkBeads( );
    Variance[i] = Merge(DecodingMap, IntensityArray);
    IF(Variance[i] < MinVariance){
        MinVariance = Variance[i];
        MinVarianceLocation = i;
    }
};
WriteAssayData(MinVarianceLocation, AssayDataRecord);   /** Save
Location **/
```

Correction for Multiple Scattering Effects. Unless suspended in specially selected density matching fluids which generally will be incompatible with bioanalytical assays of interest, polymeric, ceramic or other microparticles will exhibit strong scattering of visible light so that multiple scattering effects are readily observed in planar assemblies and arrays of such particles. For example, fluorescence emitted by a microparticle within such a close-packed planar array is diffracted by its nearest neighbors and possibly its more distant neighbors, a source of potential error in overestimating assay signals. This effect is strongly dependent on interparticle distance and may be diminished or eliminated by appropriate array and substrate design as well as choice of illumination and collection optics.

In addition, the system herein also offers a method of correcting for the effects of multiple scattering on the intensity distribution recorded from subpopulations of beads within a planar array. As with the MVM algorithm, this method takes advantage of the random spatial distribution of different bead types throughout the array. Randomly placed "blank" beads, drawn from a subpopulation that is at most weakly fluorescent for purposes of encoding, serve as local "antennae" to establish a random sample of excess fluorescence produced by way of diffraction by the nearest neighbor configurations encountered within the array. To correct for the principal global effect of multiple scattering on assay signals recorded from a random encoded array, the variance of this excess fluorescence signal is subtracted from the intra-population variance of all subpopulations.

III Transmission of Image Data Records

III.1 Identifying and Tracking Bead Arrays

As described in U.S. patent application Ser. Nos. 10/238, 439, and 10/365,993, entitled: "Encoded Random Arrays and Matrices" (the specification corresponding to WO 01/20593), incorporated herein by reference, and as further elaborated herein in Sections II.2.1 and II.2.2, each bead array generates its own unique ID ("Intrinsic ChipID" or "ChipID") and can be identified. This ChipID may be physically or logically linked to a CarrierID. For example, multiple bead arrays may be mounted on a multichip carrier comprising a bar code which is capable of recording the identity of each of the bead arrays. The CarrierID is tracked in the course of producing bead arrays and also is tracked in the course of acquiring, processing and analyzing assay images using the system of the invention. The IntrinsicChipID may be linked to a CarrierID, and to a further assigned ChipID which may be appended to the CarrierID ("Appended ChipID") or may be otherwise physically linked to the CarrierID. Unless specifically indicated below, the ChipID shall be understood to refer to Intrinsic ChipID or Appended ChipID.

Samples of interest for chemical analysis including samples collected from patients for clinical or other testing, also may be given a sample or patient ID, e.g., in the form of a barcode which may be tracked along with the CarrierID using a barcode scanner. In addition, methods of intra-analyte molecular labeling have been previously disclosed. For these purposes, the addition of unique molecular external labels or internal labels, for example in the form of a DNA fingerprints, may be considered. Such labels and associated methods have been described in U.S. patent Ser. No. 10/238,439. Information derived from the examination of these molecular labels may be entered into decoding and/or assay image records by the system herein to minimize sample handling error and to facilitate the secure exchange of information, as elaborated herein below.

III.2 Transmission Protocols

Figure 10A:
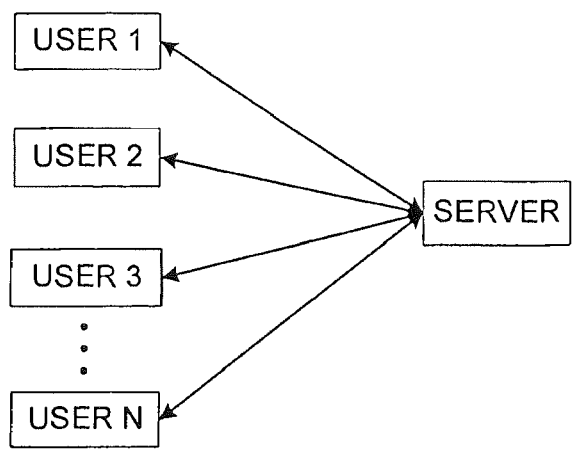
FIG. 10A is an illustration of a two-party, multiple-user, data exchange.
Figure 10B:
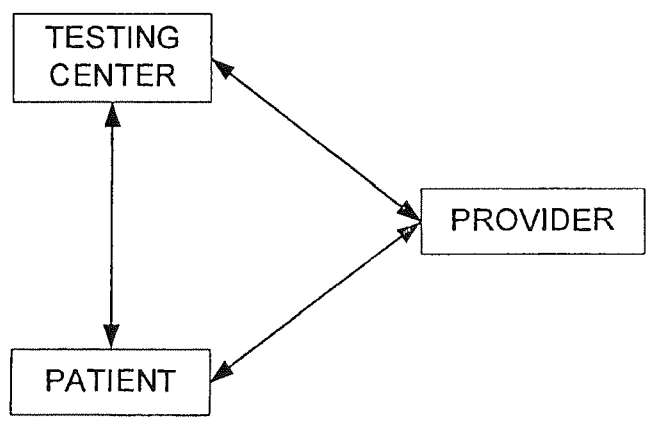
FIG. 10B illustrates a three-party data exchange, where one party is the patient.

In one embodiment, an assay image may be submitted for analysis by transmission over a network connection to a central location. Software available on centrally located servers, in one embodiment involving the ANALYZER described herein, completes the analysis and makes results of the analysis available to authorized users for retrieval. The analysis-server model provides protocols governing exchange of information in one or more two party transactions between one or more users and a central server where data is analyzed (FIG. 10a), and further provides protocols governing the exchange of information in three-party transactions, involving patient, to provider to a testing center where data is analyzed and assay results are recorded (FIG. 10b). A three-party transaction may also involve a recipient, a mediator and a provider of information.

This model offers several advantages to users as well as suppliers of molecular diagnostics, particularly when instrumentation distributed to field locations is easy to use and maintain, while the analysis of the data obtained using the instruments is complex. To the users' benefit, the requirement for designated staff with the training and expertise to install, master and operate analytical software is eliminated. Rapid turn-around of even advanced data analysis is ensured by access to rapid network connections even in remote locations at a doctor's office or patient site. Suppliers benefit from the reduction in cost associated with the logistics of providing extensive technical software support while providing high-speed analysis on dedicated server hardware. In general, the analysis service provider, equipment manufacturer and assay developer all may be distinct parties. Additional parties may participate in certain transactions. For example, the manufacturer of the chips and arrays, and the analysis service provider, may not be the same party.

The system herein provides for an analysis server model invoking transaction protocols such as those elaborated below that ensure the secure exchange of private information created, for example, in genetic analysis—an issue of wide concern. Additional services, such as advanced analysis in the form of binding pattern matching via database searches or data archiving, are readily integrated. In one embodiment, the analysis server model applies to assays producing data in the form of images and the analysis of interest relates to the analysis and archiving of images.

In one embodiment of such a transaction, the exchange of information may relate to the completion of analytical chemical, biochemical and diagnostic test, and the participating recipient, intermediary and provider of the information of interest. (e.g., personal genetic information) may correspond to patient, testing center and (data) analysis provider, respectively. Protocols are set forth for the secure creation, exchange and storage of information Transaction Protocols Pattern Matching via Access to "Fingerprint" Database. A pharmaceutical company researcher ("CLIENT") submits data recorded from an assay performed in an array format to probe the interaction between a set of immobilized proteins ("receptors") and a second set of proteins or ligands provided in a solution that is brought in contact with the receptor array. The data may be in the form of a decoded assay data record as described herein. Intensities—recorded from bead arrays or from other arrays, including "spotted" arrays—reflect a certain pattern of interactions between receptors and ligands. Alternatively, the data may represent a pattern of expression levels for a set of designated genes of interest that may indicate an individual patient's response to treatment or may indicate a toxicology profile or may indicate the response triggered by a compound of interest that is to mimic the action of a known drug, said action being characterized on a molecular level by said expression pattern.

The two-party transaction between PROVIDER and CLIENT is performed in accordance with a protocol that preserves the anonymity of the CLIENT and simply permits the CLIENT to search a PROVIDER database for matching the interaction pattern or expression pattern with a unique pattern (or "fingerprint").

Advanced Services. Once decoded assay results are in hand, additional analysis may be optionally performed. In the simplest instance, statistical measures such as mean or variance are readily evaluated over each of the subsets. More generally, the presence of characteristic "patterns" of receptor-ligand interaction may be ascertained Such patterns may be indexed and stored in a searchable database to provide the basis for assay interpretation. This in turn will facilitate tracking and interpretation of disease histories and clinical trial results and aid in the identification of molecular identifiers and features ("genotype") associated with clinical pathology ("phenotype").

File Serving: Authenticated Remote Access to Decoding Image.—Decryption of the message contained within the assay image by application of the key represented by the decoding image groups intensities in accordance with bead type is provided. Following bead array assembly, the decoding image is analyzed to derive a temporary ChipID representing a portion of the complete ChipID, based, for example, on the first row or column of the decoding image. The ChipID is stored, the temporary ChipID is transmitted to the user as a password for access to the database and retrieval of the full decoding image. In certain situations, it may be advantageous to the user not to download the full decoding image. For example, if assay results are negative, conclusions about a set of tested receptor-ligand interactions may be reached without decryption.

Alternatively, assay images may be uploaded to the server for additional analysis or archiving. Incoming assay images are linked to stored decoding images by matching temporary and full ChipID codes.

In this file server model, fees may be charged in accordance with the volume of transactions on a single transaction basis or on a subscription basis in accordance with pricing models practiced in the application server market.

A Two-Party Transaction Relating to the Analysis of Encrypted Assay Data.

The following two-party transaction (FIG. 10a) illustrated here using an embodiment in the form of custom bead arrays, invokes an encrypted covering to ensure that the identity of compounds in the assay remain private.

For example, a pharmaceutical company researcher ("CLIENT") provides to the custom bead array provider who, in this example, also is the analysis service provider ("PROVIDER"), a library of compounds to be subjected to on-chip assays in labeled containers with instructions to create an encrypted covering by simply recording the container labels corresponding to specific bead types. For example, "compound in container labeled A anchored to bead tag T1." The identity of compounds within labeled containers is known only to CLIENT. In a preferred embodiment, a unique set of bead tags is selected for a specific client to minimize mishandling or inadvertent swapping of compound libraries.

The two-party transaction between PROVIDER and CLIENT is performed in accordance with the following protocol:

Provider—Provide Bead Array with Unique ChipID
Create encrypted covering by attaching designated compounds to "tagged" beads
Create array encoding by assembling pooled beads into an array
Decode array configuration
Establish ChipID. In a preferred embodiment, the ChipID is derived from the array configuration
Optionally, store ChipID in non-volatile memory to be packaged along with bead array chip
Create a public database record ("Key") of the form (ChipID, Encrypted Covering)
Send bead array chip in assay cartridge (with ChipID) to Client
CLIENT—Perform Assay and Transmit Assay Image
Receive assay cartridge from Provider
Place analyte solution into assay cartridge and perform assay
Record ChipID. In one embodiment, use a chip carrier containing ChipID in electronic representation in conjunction with an electronic reader and the array imaging system such that the ChipID, read out from the assay chip, is recorded and stored, and thus unambiguously linked, with the encrypted message in a public record (ChipID/Public, Encrypted Message/Public)
Record assay image and create assay data record ("Encrypted Message")
Send combination of ChipID and Encrypted Message to PROVIDER for analysis
Provider—Perform Image/Data Analysis
Receive public record (ChipID, Encrypted Message) from CLIENT
Strip ChipID and check database for matching record (ChipID, Encrypted Covering) Use ChipID to decode message, thereby creating a profile. In one embodiment, the profile representing the decoded message has the form $\{<I>_k, 1 \leq k \leq n\}$, where the $<I>_k$ represent intensities averaged over all beads of tag type k, tags being uniquely associated with a specific compound in accordance with the encrypted covering
Create updated database record (ChipID, Encrypted Covering, Profile)
Provider—Transmit Profile
Supply database record (ChipID, Encrypted Covering, Profile) for retrieval by CLIENT.

A Three-Party Transaction for the Secure Exchange of Genetic Information. By generating, either concurrently with the completion of genetic analysis or by concurrent analysis of tagging molecules added to patient samples, a molecular ED such as a DNA fingerprint (as described in U.S. patent application Ser. No. 10/238,439) that is embedded within the assay image, the methods of the present invention create an unambiguous link between a chip ID ("IntrinsicChipID") derived from the configuration of a random encoded bead array and a unique genetic ID, thereby not only minimizing the possibility of error in sample handling but also enabling verification of assay results and securing confidential genetic information in the course of two-party or multi-party transactions, as elaborated below for a three-party transaction.

Figure 10C:
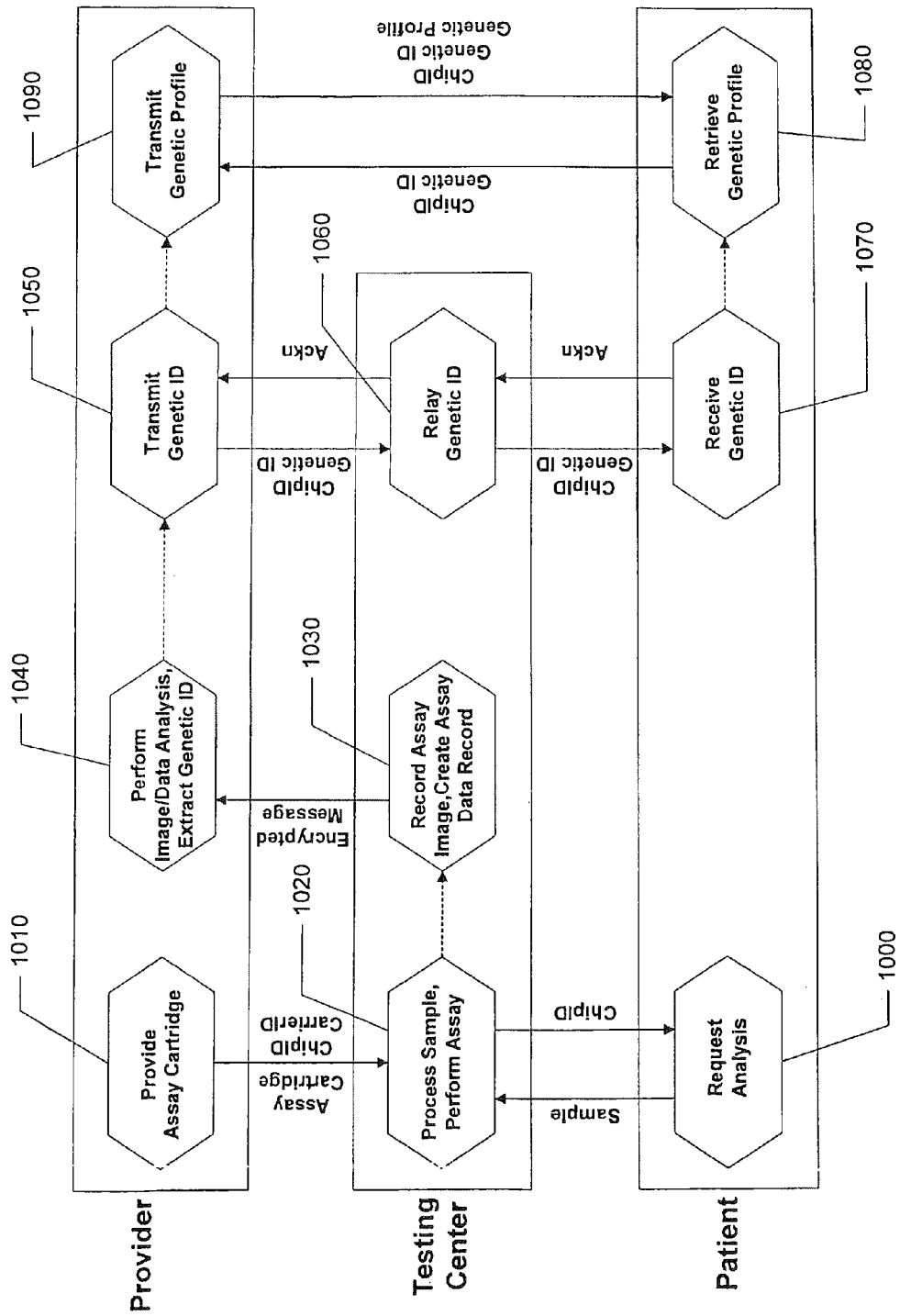
FIG. 10C illustrates more specifically a secure data transaction between three parties, where one party is the patient.
Figure 11A:
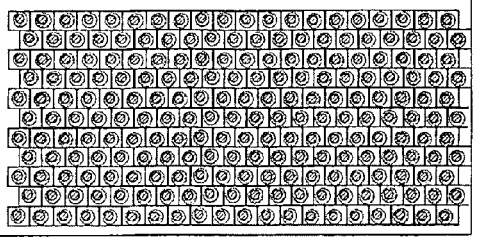
FIGS. 11A to 11D depict the DECODER Graphical User Interface (GUI) illustrating steps in the course of processing a decoding image.
Figure 11B:
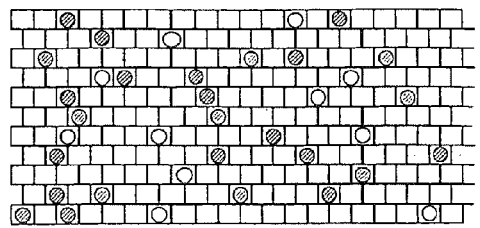
Figure 11C:
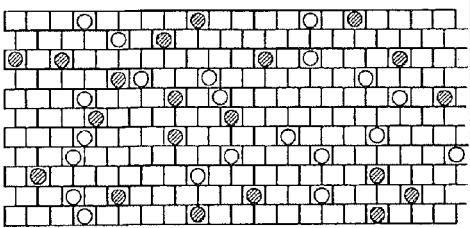
Figure 11D:
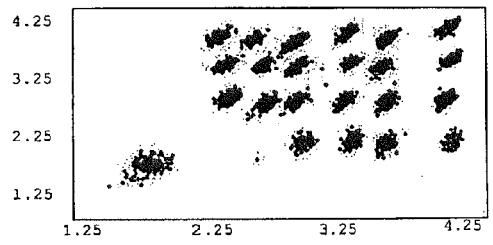

The process illustrated in FIG. 10C using a preferred embodiment in the form of custom bead arrays packaged on a carrier within a fluidic assay cartridge ensures the confidentiality of personal genetic information. Specifically, a three-party transaction between custom bead array provider who, in this example, also is the analysis service provider ("PROVIDER"), an intermediary or facilitator such as an assay, service provider ("TESTING CENTER") and user ("PATIENT") may be organized as follows to ensure privacy of information generated by genetic testing.

In this protocol, transactions between PROVIDER and TESTING CENTER and between TESTING CENTER and PATIENT involve public records that are identified by the ChipID. A separate transaction between PROVIDER and PATIENT involves the private information in the form of the genetic profile. The protocol below ensures that the identity of the PATIENT is concealed from PROVIDER: the PATIENT is identified only by the genetic ID presented for authentication in the final retrieval of genetic information. On the other hand, in the protocol below, genetic information is made available—by way of a "Relay" step—to the TESTING CENTER—or a designated physician or genetic counselor—for communication to the PATIENT.

The three-party transaction (FIG. 10C) between PROVIDER, TESTING CENTER and PATIENT is carried out in accordance with the following protocol.

Provider—Provide Encoded Bead Array Chip with Unique ChipID
Create covering by attaching probe molecules to color-encoded beads
Create array encoding by assembling pooled beads into an array
Decode configuration to establish ChipID
Optionally, store ChipID in non-volatile memory to be packaged along with bead array chip
Create a database record ("Key") of the form (ChipID/Public, Covering/Private)
Send packaged chip (with ChipID) to TESTING CENTER
PATIENT—Request Analysis
Submit sample to TESTING CENTER
Receive ChipID from TESTING CENTER
TESTING CENTER—Perform Assay
Receive assay cartridge from PROVIDER
Collect sample from PATIENT into assay cartridge
Send ChipID to PATIENT
Complete sample preparation and perform genetic analysis
TESTING CENTER—Record Assay Image and Transmit Assay Data Record
Record assay image with embedded GeneticID ("Encrypted Message")
Send combination of ChipID and Encrypted Message to PROVIDER for analysis. In a preferred embodiment, use a chip carrier containing ChipID in electronic representation in conjunction with an electronic reader and an image acquisition system under general processor control such that the ChipID, read out from the assay chip, is recorded and stored, and thus unambiguously linked, with the encrypted message in a public record (ChipID/Public, Encrypted Message/Public)

For later verification: store assay cartridge, optionally containing patient blood sample Provider—Perform Image/Data Analysis Receive public record (ChipID/Public, Encrypted Message/Public) from TESTING CENTER Strip ChipID and check database for matching decoding data record (ChipID/Public, Covering/Private)

Use covering to fully decode message identifying genetic profile and embedded GeneticID In one embodiment, the decoded message has the form of intensities, $\{<I>_k, 1 \leq k \leq n\}$, averaged over beads of the same type, each type uniquely identifying a specific probe molecule; other representations also are available as discussed herein.

Extract GeneticID from decoded assay data record image as the subset of intensities $<I>_k$ corresponding to ID-specific probes Create updated database record (ChipID/Public, Covering/Private, GenID/Public, GenProfile/Private)

Provider—Transmit Genetic ID

Send (ChipID/Public, GenID/Public) to Testing Center for transmission to Patient PATIENT—Receive Genetic ID and Retrieve Genetic Profile (1080)

Using (ChipID/Public, GenID/Public), query Provider database

Provider—Transmit Genetic Profile (1090)

Authenticate GenID to authorize retrieval of private genetic profile from database If and only if, authentication confirmed, retrieve (ChipID/Public, Covering/Private, GenID/Public, GenProfile/Private)

Supply database record (GenID/Public, GenProfile/Private) for retrieval by PATIENT Using an assay cartridge, a physical linkage can be created between patient sample, assay cartridge and BeadChip with associated ChipID while the embedded genetic ID creates a physical linkage between genetic identity and genetic profile as an inherent part of the assay. Verification is then always possible by retesting. The physical and logical linkages created by the methods of the present invention between patient sample, ChipID and genetic profile with embedded genetic ID eliminate common sources of error in genetic testing such as switching of patient samples.

Other transaction protocols may be devised using data structures of the type introduced in the foregoing example, to ensure that only the PATIENT has access to genetic (or other) information created in an assay performed at the TESTING CENTER. For example, in one embodiment of the present invention, the PATIENT already may be in possession of his/her GeneticID prior to initiating a three-party transaction. In that case, the steps of transmitting, relaying and receiving GeneticID (FIG. 10c, 1050, 1060, and 1070) may be eliminated. Instead, the PATIENT directly requests transmission of the genetic profile from the PROVIDER—access to the relevant database may be authenticated by comparing the Genetic ID used in the request with the Genetic ID extracted from the genetic profile.

Decoded assay data records may be archived. Archived decoded assay data records would be accessed only by those in possession of a GeneticID or equivalent key embedded in the decoded assay data record. That is, the database of archived records would be searched by rapid cross-correlation with the authentication code.

More generally, the following three-party protocol ensures that only the PATIENT (or his/her designee, such as a physician) who initiates a testing procedure is in possession of private information created in the test performed at the TESTING CENTER and analyzed by the application service PROVIDER. The TESTING CENTER has no access to the private information and PROVIDER has no knowledge of the identity or particulars of the PATIENT. The PATIENT, having requested and having been assigned, a ChipID and SampleID, requests, directly from the PROVIDER, a confidential authentication key. In one embodiment, this is accomplished by access to the PROVIDER site, for example by a remote login. If the confidential authentication key generated by the combination of ChipID and SampleID is taken by a third party, the PATIENT will have immediate knowledge that the confidential authentication key may be at risk of disclosure to a third party. The PATIENT may be able to request a new SampleID before providing a new biological sample to the TESTING CENTER. Software then assigns a randomly selected encrypted personalized authentication key to the combination of ChipID/SampleID presented in the request. Only one such assignment is permitted. In one embodiment, the encrypted authentication key has the form of a "cookie" that is placed in a hidden directory on the hard drive or other storage device of the requesting machine so that only that machine is authenticated for future retrieval of testing data from the PROVIDER. The PATIENT will ensure the integrity of the process: should an unauthorized party, for example, at the TESTING CENTER, attempt to acquire an authentication key, the subsequent attempt by the PATIENT to do so would fail, alarming the PATIENT to a possible breach in protocol. In one embodiment, the encrypted authentication key assigned to the requesting ChipID/Sample ID combination will be the IntrinsicChipID, or information embedded therein. In one embodiment, the random string of integers indicating vertex positions of a designated specific bead type within the BeadChip may be used. Following submission by the TESTING CENTER of the Assay Data Record, identified by a ChipID, for analysis, the PROVIDER combines the Assay Data Record with the Decoding Data Record corresponding to the submitted ChipID so as to create a decoded Assay Data Record from which specific embedded information such as a genetic profile may be extracted by "De-Covering", that is, application of the Covering to identify specific probes within the array as previously elaborated herein. This information is made available for retrieval by the PATIENT using the encrypted authentication key previously assigned to the ChipID/Sample ID combination. In one embodiment, only the machine previously endowed with a "cookie" will be permitted to access the database containing the requested information. This protocol ensures that the TESTING CENTER knows only the identity of the PATIENT but not the information such as a genetic profile extracted from the assay while the PROVIDER knows the information such as a genetic profile but not the identity of the PATIENT.

It will be apparent to those skilled in the art that the foregoing specific instances of two-party and three-party transactions merely illustrate the concepts involved which are applicable to a wider range of applications.

Pricing Strategies. The analysis server model of the present invention provides "fee-for-service"—in a single transaction format or in subscription pricing format—in which the initial cost of instrumentation as well as the recurring cost for disposable items can be absorbed in the charges for one or more of a palette of services. This has the advantage of eliminating user capital expenditures. The charges are for analysis, not for enabling instrumentation or assay components.

EXAMPLES

Example 1

Acquiring and Processing Decoding Image(s)

FIG. 11 illustrates the processing steps performed by the DECODER. Displayed in a Graphical User Interface (GUI) (1100) are three images, namely: a Brightfield image (1110), a green fluorescence image (1120) and a blue fluorescence image (1130). Grids, extracted and aligned by the DECODER, also are displayed. Also displayed is a scatter plot (1140) produced by the DECODER from the intensities in green and blue fluorescence images.

Example 2

Constructing Decoding Map

Figure 12:
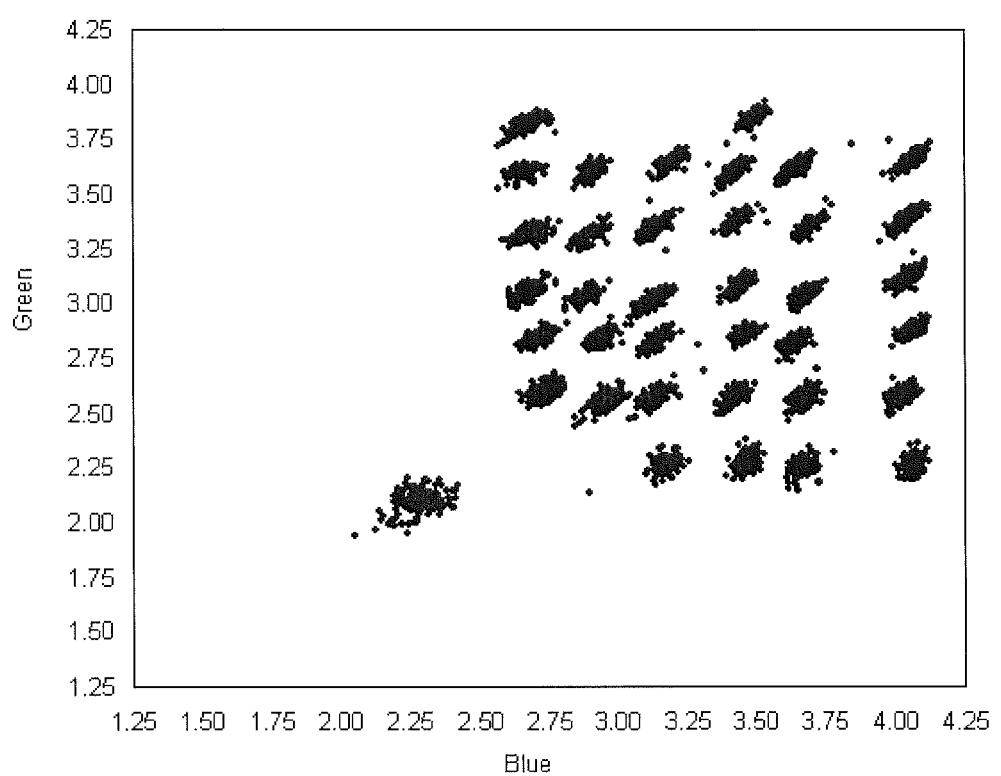
FIG. 12 illustrates a constructed Decoding Map.

FIG. 12 illustrates the construction of the 2D decoding map by the ANALYZER which may be integrated with the DECODER whose GUI is shown (1200). The map of the present example is composed of 33 clusters (1210), each of which is assigned a unique tag index. This is displayed for each cluster along with the number of beads contained in that cluster. For example, cluster 1 contains 101 beads.

Example 3

Acquiring and Processing Assay Image(s)

FIG. 13 illustrates the processing steps performed by the READER. Displayed in a GUI (1300) are three images, namely: a Brightfield image (1310), a fluorescence image (1320). Grids, extracted and aligned by the READER, also are displayed.

Example 4

Analyzing Images and Extracting Representations

FIG. 14 illustrates the Decoded Assay Data Record in two sections, namely: a text display (1400) listing assay signals extracted from the assay data record along with tag indices assigning each signal to a cluster and hence to a color code; and, a bar graph display (1420) of data from the Decoded Assay Data Record.

It should be understood that the foregoing examples and descriptions are exemplary only and not limiting, and that all methods and processes set forth are not to be limited to any particular order or sequence, unless specified, and that the scope of the invention is defined only in the claims which follow, and includes all equivalents of the claims.

The invention claimed is:

1. A method of conducting an assay and analyzing results therefrom at separate locations, comprising:
conducting an assay on a patient sample by contacting a uniquely encoded array of receptors with the patient sample and determining if the patient sample comprises any ligands that interact with the receptors by analyzing an assay image for optical signatures that are associated with receptor-ligand interactions and recording the assay image in a first processor, wherein the array is decoded by a second processor at a location other than the location at which the assay is conducted, wherein the first and second processors communicate by way of a data network.

2. The method of claim 1, wherein the uniquely encoded array is an array of encoded beads, wherein different beads have different receptors associated therewith.

3. The array of claim 2, wherein the encoding of the beads is with different colors.

4. The array of claim 1, wherein the optical signatures from the receptors result from the association of a fluorescent entity with the ligand attached to the receptor.

5. The method of claim 1, further comprising obtaining the patient sample, wherein the obtaining and conducting steps are conducted at separate locations.

6. The method of claim 1, further including the step of providing the one or more images of the uniquely encoded array of receptors recorded before conducting the assay to the location at which the assay was conducted, to the patient, or to another location.

7. The method of claim 1, further including the step of providing the one or more images of the uniquely encoded array of receptors recorded after conducting the assay to the location at which the assay was conducted, to the patient, or to another location.

8. The method of claim 1, wherein the assay relates to patient genetic information or to information about certain proteins or antibodies in a patient.

9. The method of claim 1, wherein the assay relates to the presence of tumor markers, markers associated with autoimmune disorders, blood-borne viruses, therapeutic drugs, genetic mutations associated with genetic diseases, polymorphisms, or other chromosomal abnormalities in the patient sample.

10. The method of claim 1, wherein the assay is a multiplexed assay.

11. The method of claim 1, further including the step of transmitting the assay image, one or more images of the uniquely encoded array of receptors, or both to a location where the images are archived.

12. The method of claim 1, wherein the identity of the patient from whom the patient sample is obtained is available only to authorized parties.

13. The method of claim 11, wherein all images are transmitted with an encryption key so that an image can be accessed only by an authorized party with access to the encryption key.

14. The method of claim 13, wherein the encryption key is a pattern of the encoded array of receptors.

15. The method of claim 13, wherein the encryption key is a bar code or other unique identifier code.

16. A method comprising:
obtaining an assay image recorded in a first processor, wherein the assay image is an image arising from an assay conducted on a patient sample by contacting a uniquely encoded array of receptors with the patient sample, and wherein the assay image can be analyzed for optical signatures that are associated with interactions between ligands present in the patient sample and receptors of the array; and
decoding the array using a second processor at a location other than the location at which the assay is conducted, wherein the first and second processors communicate by way of a data network.

17. The method of claim 16, wherein the uniquely encoded array is an array of encoded beads, wherein different beads have different receptors associated therewith.

18. A method comprising:
   obtaining an assay image recorded in a first processor, wherein the assay image is an image arising from an assay conducted on a patient sample by contacting a uniquely encoded array of receptors with the patient sample, wherein the assay image provides optical signatures that are associated with interactions between ligands present in the patient sample and receptors of the array;
   obtaining a decoding image, wherein the decoding image identifies the receptors at each position of the array; and
   analyzing the results of the assay by combining the assay image and decoding images, wherein the analyzing is done using a second processor at a location other than the location at which the assay is conducted, wherein the first and second processors communicate by way of a data network.

19. The method of claim 18, wherein the uniquely encoded array is an array of encoded beads, wherein different beads have different receptors associated therewith.

* * * * *